(12) United States Patent
Maienfisch et al.

(10) Patent No.: US 7,737,261 B2
(45) Date of Patent: Jun. 15, 2010

(54) AVERMECTIN B1 AND AVERMECTIN B1 MONOSACCHARIDE DERIVATIVES HAVING AN ALKOXYMETHYL SUBSTITUENT IN THE 4"- OR 4'-POSITION

(75) Inventors: Peter Maienfisch, Basel (CH); Fiona Murphy Kessabi, Basel (CH); Jérôme Cassayre, Basel (CH); Laura Quaranta, Basel (CH); Thomas Pitterna, Basel (CH); Ottmar Franz Hueter, Basel (CH); Pierre Jung, Basel (CH)

(73) Assignee: Syngenta Corp Protection, Inc., Greensboro, NC (US)

( * ) Notice: Subject to any disclaimer, the term of this patent is extended or adjusted under 35 U.S.C. 154(b) by 1043 days.

(21) Appl. No.: 10/539,274

(22) PCT Filed: Dec. 19, 2003

(86) PCT No.: PCT/EP03/14613

§ 371 (c)(1),
(2), (4) Date: Mar. 9, 2006

(87) PCT Pub. No.: WO2004/056844

PCT Pub. Date: Jul. 8, 2004

(65) Prior Publication Data

US 2006/0148729 A1 Jul. 6, 2006

(30) Foreign Application Priority Data

Dec. 20, 2002 (GB) .................. 0229804.0

(51) Int. Cl.
*C07H 17/04* (2006.01)
(52) U.S. Cl. ......................... 536/7.1; 514/30
(58) Field of Classification Search ............ 536/7.1
See application file for complete search history.

(56) References Cited

U.S. PATENT DOCUMENTS

| 4,310,519 A | 1/1982 | Albers-Schonberg et al. |
| 5,112,854 A | 5/1992 | Ramsay et al. |
| 5,169,839 A * | 12/1992 | Linn et al. ............ 514/30 |
| 5,346,918 A | 9/1994 | Morisawa et al. |
| 5,411,737 A | 5/1995 | Hsu et al. |
| 5,436,355 A | 7/1995 | Demchak |
| 5,516,761 A | 5/1996 | Choi et al. |
| 5,602,107 A | 2/1997 | Choi |
| 5,604,182 A | 2/1997 | Morisawa et al. |
| 5,945,445 A | 8/1999 | Barringer et al. |
| 2004/0018993 A1 | 1/2004 | Omura et al. |
| 2004/0087519 A1 | 5/2004 | Omura et al. |
| 2005/0148520 A1 | 7/2005 | Omura et al. |

FOREIGN PATENT DOCUMENTS

| EP | 0 353 959 A2 | 2/1990 |
| EP | 0456509 | 11/1991 |
| EP | 0519731 | 12/1992 |

OTHER PUBLICATIONS

Tsukamoto, Yoshihisa et al: "Avermectin chemistry and action: ester- and ether-type candidate photoaffinity probes:"; Bioorgranic & Medicinal Chemistry (2000), 8(1), 19-26.

Shoop, W. L. et al: "Efficacy in sheep and pharmacokinetics in cattle that led to the selection of eprinomectin as a topical endectocide for cattle"; International Journal for Parasitology (1996), 26(11), 1227-1235.

Jones, Todd K. et al: "Synthesis and Biological Activity of a 4a4"-Disubstituted Avermetcins"; Journal of Agricultural and Food Chemistry (1994), 42(8), 1786-90.

* cited by examiner

*Primary Examiner*—Elli Peselev
(74) *Attorney, Agent, or Firm*—William F. Mulholland, II

(57) ABSTRACT

Avermectin B1 and avermectin B1 monosaccharide derivative compounds having an alkoxymethyl substituent in the 4"- or 4'-position; a process for preparing and using these compounds and their tautomers; pesticides whose active compound is selected from these compounds and their tautomers; and a process for preparing these compounds and compositions are provided.

3 Claims, No Drawings

AVERMECTIN B1 AND AVERMECTIN B1 MONOSACCHARIDE DERIVATIVES HAVING AN ALKOXYMETHYL SUBSTITUENT IN THE 4″ -OR 4′-POSITION

This application is a 371 of International Application No. PCT/EP2003/014613 filed Dec. 19, 2003, which claims priority to GB 0229804.0, filed Dec. 20, 2002, the contents of which are incorporated herein by reference.

The invention relates to (1) a compound of formula

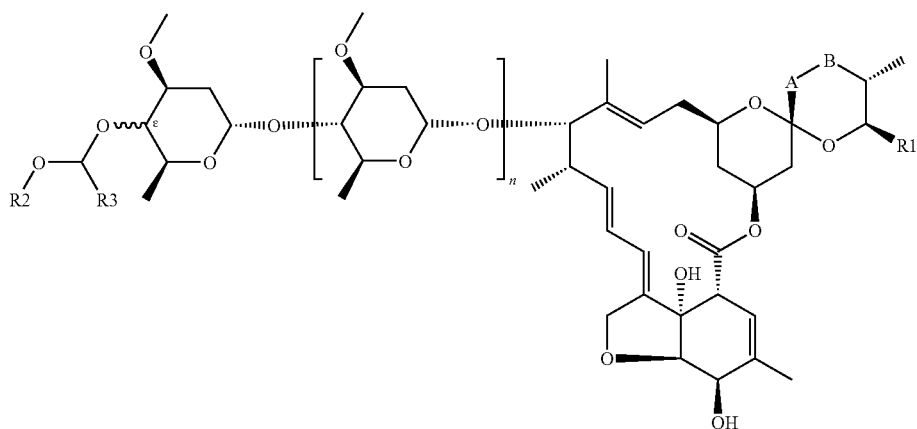

(I)

wherein n is 0 or 1;

A-B is —CH=CH— or —CH$_2$—CH$_2$—;

$R_1$ is $C_1$-$C_{12}$-alkyl, $C_3$-$C_8$-cycloalkyl or $C_2$-$C_{12}$-alkenyl;

$R_2$ is $C_1$-$C_{12}$-alkyl, $C_2$-$C_{12}$-alkenyl, $C_2$-$C_{12}$-alkinyl; or $C_1$-$C_{12}$-alkyl, $C_2$-$C_{12}$-alkenyl or $C_2$-$C_{12}$-alkinyl, which are substituted with one to five substituents selected from the group consisting of OH, halogen, CN, —N$_3$, —NO$_2$, $C_3$-$C_8$-cycloalkyl that is optionally substituted with one to three $C_1$-$C_6$-alkyl-groups, $C_3$-$C_8$-cycloalkenyl that is optionally substituted with one to three $C_1$-$C_6$-alkyl-groups, norbornylenyl, $C_3$-$C_8$-halocycloalkyl, $C_1$-$C_{12}$-alkoxy, $C_1$-$C_6$-alkoxy-$C_1$-$C_6$-alkoxy, $C_3$-$C_8$-cycloalkoxy, $C_1$-$C_{12}$-haloalkoxy, $C_1$-$C_{12}$-alkylthio, $C_3$-$C_8$-cycloalkylthio, $C_1$-$C_{12}$-haloalkylthio, $C_1$-$C_{12}$-alkylsulfinyl, $C_3$-$C_8$-cycloalkylsulfinyl, $C_1$-$C_{12}$-haloalkylsulfinyl, $C_3$-$C_8$-halocycloalkylsulfinyl, $C_1$-$C_{12}$-alkylsulfonyl, $C_3$-$C_8$-cycloalkylsulfonyl, $C_1$-$C_{12}$-haloalkylsulfonyl, $C_3$-$C_8$-halocycloalkylsulfonyl, —NR$_4$R$_6$, —X—C(=Y)—R$_4$, —X—C(=Y)—Z—R$_4$, —P(=O)(OC$_1$-$C_6$-alkyl)$_2$, aryl, heterocyclyl, aryloxy, arylthio and heterocyclyloxy; wherein the aryl, heterocyclyl, aryloxy, arylthio and heterocyclyloxy groups are optionally—depending on the substitution possibilities on the ring—substituted with one to five substituents selected form the group consisting of OH, Halogen, CN, NO$_2$, $C_1$-$C_{12}$-alkyl, $C_3$-$C_8$-Cycloalkyl, $C_1$-$C_{12}$-Haloalkyl, $C_1$-$C_{12}$-alkoxy, $C_1$-$C_{12}$-Haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, Si($C_1$-$C_{12}$-alkyl)$_3$, —X—C(=Y)—R$_4$, —X—C(=Y)—Z—R$_4$, aryl, aryloxy, heterocyclyl and heterocyclyloxy; or $R_3$ is aryl, heterocyclyl $C_3$-$C_8$-cycloalkyl, $C_3$-$C_8$-cycloalkenyl; or aryl, heterocyclyl $C_3$-$C_8$-Cycloalkyl or $C_3$-$C_8$-Cycloalkenyl, which are optionally—depending on the substitution possibilities on the ring—substituted with one to five substituents selected from the group consisting of OH, halogen, CN, NO$_2$, $C_1$-$C_{12}$-alkyl, $C_3$-$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, dimethylamino-$C_1$-$C_6$-alkoxy, $C_2$-$C_8$-alkenyl, $C_2$-$C_8$-alkinyl, methylendioxy, aryl, aryloxy, heterocyclyl and heterocyclyloxy;

$R_3$ is H, $C_1$-$C_{12}$-alkyl or $C_1$-$C_{12}$-alkyl which is substituted with one to five substituents selected from the group consisting of OH, halogen, CN, —N$_3$, —NO$_2$; $C_3$-$C_8$-Cycloalkyl that is optionally substituted with one to three $C_1$-$C_6$-alkyl groups; norbornylenyl-; $C_3$-$C_8$-Cycloalkenyl that is optionally substituted with one to three methyl groups; $C_3$-$C_8$-halocycloalkyl, $C_1$-$C_{12}$-alkoxy, $C_1$-$C_6$-alkoxy-$C_1$-$C_6$-alkoxy, $C_3$-$C_8$-cycloalkoxy, $C_1$-$C_{12}$-haloalkoxy, $C_1$-$C_{12}$-alkylthio, $C_3$-$C_8$-cycloalkylthio, $C_1$-$C_{12}$-haloalkylthio, $C_1$-$C_{12}$-alkylsulfinyl, $C_3$-$C_8$-cycloalkylsulfinyl, $C_1$-$C_{12}$-haloalkylsulfinyl, $C_3$-$C_8$-halocycloalkylsulfinyl, $C_1$-$C_{12}$-alkylsulfonyl, $C_3$-$C_8$-cycloalkylsulfonyl, $C_1$-$C_{12}$-haloalkylsulfonyl, $C_3$-$C_8$-halocycloalkylsulfonyl, —NR$_4$R$_6$, —X—C(=Y)—R$_4$, —X—C(=Y)—Z—R$_4$, —P(=O)(OC$_1$-$C_6$-alkyl)$_2$, aryl, heterocyclyl, aryloxy, arylthio and heterocyclyloxy; wherein the aryl, heterocyclyl, aryloxy, arylthio and heterocyclyloxy groups are optionally—depending on the substitution possibilities on the ring—substituted with one to five substituents selected form the group consisting of OH, Halogen, CN, NO$_2$, $C_1$-$C_{12}$-alkyl, $C_3$-$C_8$-Cycloalkyl, $C_1$-$C_{12}$-Haloalkyl, $C_1$-$C_{12}$-alkoxy, $C_1$-$C_{12}$-Haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, Si($C_1$-$C_{12}$-alkyl)$_3$, —X—C(=Y)—R$_4$, —X—C(=Y)—Z—R$_4$, aryl, aryloxy, heterocyclyl and heterocyclyloxy; or $R_2$ and $R_3$ together are a three- to seven-membered alkylen- or a four- to seven-membered alkenylenbridge, wherein one or two CH$_2$-groups may independently of each other be replaced by a group —C(=O)—, —C(=S)—, O, S, —NR$_5$—, —OC(=O)—O—, —OC(=O)S—, —OC(=O)N(R$_5$)—, —C(=O)O—, —C(=O)S—, —C(=O)N(R$_5$)—, —N(R$_5$)C(=O)S—, —N(R$_5$)C(=O)N(R$_5$)—, and wherein the alkylene or alkenylenbridge may be independently of each other substituted with one or two substituents selected from the group consisting of $C_1$-$C_4$-alkyl, which is optionally substituted with one to five substituents independently selected from the group consisting of OH, Halogen, CN, NO$_2$, —N$_3$ and $C_1$-$C_4$-alkoxy;

X is O, $NR_5$ or a bond;

Y is O or S;

Z is O, S or $NR_5$ $R_4$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution possibilities—optionally substituted in the ring with one to five substituents selected from the group consisting of halogen, $C_1$-$C_6$-alkoxy, $C_1$-$C_6$-haloalkyl and $C_1$-$C_6$-haloalkoxy;

$R_5$ is H, $C_1$-$C_8$-alkyl, $C_3$-$C_8$-cycloalkyl, $C_2$-$C_8$-alkenyl, $C_2$-$C_8$-alkinyl, benzyl or —C(=O)—$C_1$-$C_{12}$-alkyl;

$R_6$ is H, $C_1$-$C_{12}$-alkyl which is optionally substituted with halogen, $C_1$-$C_6$-alkoxy, CN, $C_2$-$C_8$-alkenyl, $C_2$-$C_8$-haloalkenyl, $C_2$-$C_8$-alkinyl, $C_1$-$C_{12}$-Haloalkenyl, —X—C(=Y)—$R_9$, —X—C(=Y)—Z—$R_9$, —$SO_2$—$R_9$, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution possibilities—optionally substituted in the ring with one to five substituents selected from the group consisting of halogen, $C_1$-$C_6$-alkoxy, $C_1$-$C_6$-haloalkyl or $C_1$-$C_6$-haloalkoxy; or $R_4$ and $R_6$ together are a three- to five membered alkylene bridge, wherein one of the methylene groups may be replaced by O, S or $SO_2$; and $R_9$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution possibilities—optionally substituted in the ring with one to five substituents selected from the group consisting of halogen, $C_1$-$C_6$-alkoxy, $C_1$-$C_6$-haloalkyl and $C_1$-$C_6$-haloalkoxy;

and, where applicable, to E/Z isomers, mixtures of E/Z isomers and/or tautomers, in each case in free form or in salt form;

with the proviso, that the compound is not an Avermectin B1 derivative wherein n is 1, $R_3$ is H, and $R_2$ is —$CH_2$—$CH_2$—$OCH_3$ or —$CH_2$—$CH_2$—O-phenyl; is not the B1 derivative wherein n is 2, $R_3$ is H, and $R_2$ is —$CH_2$—$CH_2$—O-phenyl; and is not the B1 derivative wherein A-B is —$CH_2$—$CH_2$—, n is 1, $R_3$ is H, and $R_2$ is —$CH_2$—$CH_2$—$OCH_3$;

to a process for the preparation of and to the use of those compounds and their isomers and tautomers; to starting materials and intermediates for the preparation of the compounds of formula (I); to pesticidal compositions in which the active ingredient has been selected from the compounds of formula (I) and their tautomers; to a method for preparing the said compositions; and to a method of controlling pests using those compositions.

Hereinbefore and hereinafter, the bond marked by the symbol ⁓ in formulae (I), (II) and (IV) indicates that at the ε-position the S- as well as the R-isomer is meant.

Certain macrolide compounds are proposed for pest control in the literature. The biological properties of those known compounds are not entirely satisfactory, however, for which reason there is a need to provide further compounds having pesticidal properties, especially for the control of insects and members of the order Acarina. That problem is solved according to the invention by the provision of the present compounds of formula (I).

The compounds claimed according to the invention are derivatives of avermectin. Avermectins are known to the person skilled in the art. They are a group of structurally closely related pesticidally active compounds which are obtained by fermentation of a strain of the microorganism *Streptomyces avermitilis*. Derivatives of avermectins can be obtained via conventional chemical syntheses.

The avermectins obtainable from *Streptomyces avermitilis* are designated A1a, A1b, A2a, A2b, B1a, B1b, B2a and B2b. Compounds with the designation "A" have a methoxy radical in the 5-position; those compounds designated "B" have an OH group. The "a" series comprises compounds wherein the substituent $R_1$ (in position 25) is a sec-butyl radical; in the "b" series there is an isopropyl radical in the 25-position. The number 1 in the name of a compound indicates that atoms 22 and 23 are bonded by a double bond; the number 2 indicates that they are bonded by a single bond and carbon atom 23 carries an OH group. The above designations are retained in the description of the present invention in order in the case of the non-natural avermectin derivatives according to the invention to indicate the specific structural type corresponding to natural avermectin. There are claimed according to the invention derivatives of compounds of the B1 and B2 series, more especially mixtures of derivatives of avermectin B1a, B1b, B2a and B2b or the corresponding monosaccharides having, at the 4'- or 4"-position (ε-position), either the S- or the R-configuration.

Some of the compounds of formula (I) may be in the form of tautomers. Accordingly, any reference to the compounds of formula (I) hereinbefore and hereinafter is to be understood, where applicable, as including also corresponding tautomers, even if the latter are not specifically mentioned in every case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid; with strong organic carboxylic acids, such as unsubstituted or substituted, for example halo-substituted, $C_1$-$C_4$alkanecarboxylic acids, for example acetic acid, unsaturated or saturated dicarboxylic acids, for example oxalic acid, malonic acid, maleic acid, fumaric acid or phthalic acid, hydroxycarboxylic acids, for example ascorbic acid, lactic acid, malic acid, tartaric acid or citric acid, or benzoic acid; or with organic sulfonic acids, such as unsubstituted or substituted, for example halo-substituted, $C_1$-$C_4$alkane- or aryl-sulfonic acids, for example methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example sodium, potassium or magnesium salts; or salts with ammonia or with an organic amine, such as morpholine, piperidine, pyrrolidine, a mono-, di- or tri-lower alkylamine, for example ethylamine, diethylamine, triethylamine or dimethylpropylamine, or a mono-, di- or trihydroxy-lower alkylamine, for example mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Unless defined otherwise, the general terms used hereinbefore and hereinafter have the meanings given below.

Unless defined otherwise, carbon-containing groups and compounds each contain from 1 up to and including 6, preferably from 1 up to and including 4, especially 1 or 2, carbon atoms.

Halogen—as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine.

Alkyl—as a group per se and as a structural element of other groups and compounds, such as haloalkyl, alkoxy and alkylthio—is, in each case giving consideration to the number of carbon atoms contained in the group or compound in question, either straight-chained, i.e. methyl, ethyl, propyl, butyl, pentyl, hexyl, heptyl or octyl, or branched, e.g. isopropyl, isobutyl, sec-butyl, tert-butyl, isopentyl, neopentyl or isohexyl.

Cycloalkyl—as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl.

Alkenyl—as a group per se and as a structural element of other groups and compounds—is, giving due consideration to the number of carbon atoms and conjugated or isolated double bonds contained in the group in question, either straight-chained, e.g. vinyl, allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert-pentenyl, isohexenyl, isoheptenyl or isooctenyl. Alkenyl groups having from 3 to 12, especially from 3 to 6, more especially 3 or 4, carbon atoms are preferred.

Alkynyl—as a group per se and as a structural element of other groups and compounds—is, in each case giving due consideration to the number of carbon atoms and conjugated or isolated triple bonds contained in the group or compound in question, either straight-chained, e.g. ethynyl, propargyl, 2-butynyl, 3-pentynyl, 1-hexynyl, 1-heptynyl, 3-hexen-1-ynyl or 1,5-heptadien-3-ynyl, or branched, e.g. 3-methylbut-1-ynyl, 4-ethylpent-1-ynyl, 4-methylhex-2-ynyl or 2-methylhept-3-ynyl. Alkynyl groups having from 3 to 12, especially from 3 to 6, more especially 3 or 4, carbon atoms are preferred.

Alkylene and alkenylene are straight-chained or branched bridge members, especially —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$($CH_3$)$CH_2$—$CH_2$—, —$CH_2$C($CH_3$)$_2$—$CH_2$—, —$CH_2$—CH=CH—$CH_2$— or —$CH_2$—CH=CH—$CH_2$—$CH_2$—.

Halo-substituted carbon-containing groups and compounds, such as alkyl, alkenyl, alkynyl, cycloalkyl, alkoxy or alkylthio substituted by halogen, may be partially halogenated or perhalogenated, it being possible in the case of polyhalogenation for the halogen substituents to be the same or different. Examples of haloalkyl—as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is especially phenyl, naphthyl, anthracenyl or perylenyl, preferably phenyl.

Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, tetrazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl or indazolyl, which are preferably bonded via a carbon atom; preference is given to thienyl, thiazolyl, benzofuranyl, benzothiazolyl, furyl, tetrahydropyranyl and indolyl; especially pyridyl or thiazolyl.

Within the scope of the present invention, preference is given to (2) a compound according to group (1) of formula (I) in the free form;

(3) a compound according to anyone of groups (1) or (2) of formula (I) wherein $R_3$ is H;

(4) a compound according to anyone of groups (1) or (2) of formula (I) wherein $R_3$ is $C_1$-$C_8$-alkyl;

(5) a compound according to anyone of groups (1) to (4) of formula (I) wherein $R_2$ is $C_1$-$C_8$-alkyl, especially methyl;

(6) a compound according to anyone of groups (1) to (5) of formula (I) wherein $R_2$ is $C_3$-$C_8$-alkyl, especially propyl or isopropyl;

(7) a compound according to anyone of groups (1) to (5) of formula (I) wherein $R_2$ is a branched $C_3$-$C_8$-alkyl, especially isobutyl, sec-butyl or tert-butyl;

(8) a compound according to one of groups (1) to (4) of formula (I) wherein $R_2$ is $C_1$-$C_8$-alkoxy-$C_1$-$C_8$-alkyl;

(9) a compound according to anyone of groups (1) to (4) of formula (I) wherein $R_2$ is $C_1$-$C_8$-alkyl which is substituted with one to five substituents selected from the group consisting of OH, halogen, CN, —$N_3$, —$NO_2$; $C_3$-$C_8$-cycloalkyl which is optionally substituted with one to three $C_1$-$C_6$-alkyl groups; norbornylenyl; $C_3$-$C_8$-Cycloalkenyl which is optionally substituted with one to three methyl groups; $C_3$-$C_8$-halocycloalkyl, $C_3$-$C_8$-cycloalkoxy, $C_1$-$C_{12}$-haloalkoxy, $C_1$-$C_{12}$-alkylthio, aryl, heterocyclyl, arylthio or heterocyclyloxy; wherein the aryl, heterocyclyl, arylthio and heterocyclyloxy groups are optionally—depending on the substitution possibilities on the ring—substituted with one to five substituents selected form the group consisting of OH, Halogen, CN, $NO_2$, $C_1$-$C_{12}$-alkyl, $C_3$-$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, Si($C_1$-$C_{12}$-alkyl)$_3$, —X—C(=Y)—$R_4$, —X—C(=Y)—Z—$R_4$, aryl, aryloxy, heterocyclyl and heterocyclyloxy; more especially wherein $R_2$ is $C_1$-$C_8$-alkyl which is substituted with one substituent selected from the group consisting of $C_3$-$C_8$-cycloalkylthio, $C_1$-$C_{12}$-haloalkylthio, $C_1$-$C_{12}$-alkylsulfinyl, $C_3$-$C_8$-cycloalkylsulfinyl, $C_1$-$C_{12}$-haloalkylsulfinyl, $C_3$-$C_8$-halocycloalkylsulfinyl, $C_1$-$C_{12}$-alkylsulfonyl, $C_3$-$C_8$-cycloalkylsulfonyl, $C_1$-$C_{12}$-haloalkylsulfonyl, $C_3$-$C_8$-halocycloalkylsulfonyl, —$NR_4R_6$, —X—C(=Y)—$R_4$, —X—C(=Y)—Z—$R_4$, —P(=O)(O$C_1$-$C_6$-alkyl)$_2$;

(10) a compound according to anyone of groups (1) to (4) of formula (I) wherein $R_2$ is $C_1$-$C_4$-alkyl which is substituted with one or two substituents selected from the group consisting of OH, halogen, CN, —$N_3$, —$NO_2$, $C_1$-$C_{12}$-alkylsulfinyl, $C_1$-$C_{12}$-alkylsulfonyl, $C_1$-$C_{12}$-haloalkylsulfonyl, —$NR_4R_6$, —X—C(=Y)—$R_4$, —X—C(=Y)—Z—$R_4$, aryl or heterocyclyl, wherein the aryl and heterocyclyl groups are optionally—depending on the substitution possibilities on the ring—substituted with one or two substituents selected form the group consisting of OH, Halogen, CN, $NO_2$, $C_1$-$C_4$-alkyl, —$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, Si($C_1$-$C_{12}$-alkyl)$_3$, —X—C(=Y)—$R_4$, —X—C(=Y)—Z—$R_4$, aryl, aryloxy, heterocyclyl and heterocyclyloxy;

(11) a compound according to anyone of groups (1) to (4) of formula (I) wherein $R_2$ and $R_3$ together are a three- to five-membered alkenylenbridge, wherein one two $CH_2$-group may be replaced by a group —C(=O)—, —C(=S)—, O, S or —$NR_5$—, and wherein the alkylene or alkenylenbridge may be independently of each other substituted with one or two substituents selected from the group consisting of $C_1$-$C_4$-alkyl;

(12) a compound according to anyone of groups (1) to (11) of formula (I) wherein $R_1$ is isopropyl or sec-butyl, preferably wherein a mixture of the isopropyl and the sec-butyl derivative is present;

(13) a compound according to anyone of groups (1) to (11) of formula (I) wherein $R_1$ is cyclohexyl;

(14) a compound according to anyone of groups (1) to (12) of the formula (I), in which n is 1;

(15) a compound according to anyone of groups (1) to (12) of the formula (I), in which n is 0;

(16) a compound according to anyone of groups (1) to (15) of the formula (I), in which A-B is —$CH_2$—$CH_2$—;

(17) a compound according to anyone of groups (1) to (15) of the formula (I), in which A-B is —CH=CH—;

(18) a compound according to anyone of groups (1) to (17) of the formula (I) having the R-configuration in the ϵ-position;

(19) a compound according to anyone of groups (1) to (17) of the formula (I) having the S-configuration in the ϵ-position;

(20) a compound according to anyone of groups (1) to (19) of the formula (I) with the further proviso that the compound is not the Avermectin B1 derivative wherein n is 1, and $R_2$ and $R_3$ together are unsubstituted —$CH_2$—$CH_2$—$CH_2$—$CH_2$—.

Especially preferred are the compounds of the tables.

The invention further relates to a process for the preparation of the compounds of formula (I) as defined above under (1) and, where applicable, tautomers thereof, which comprises (A) reacting a compound of formula

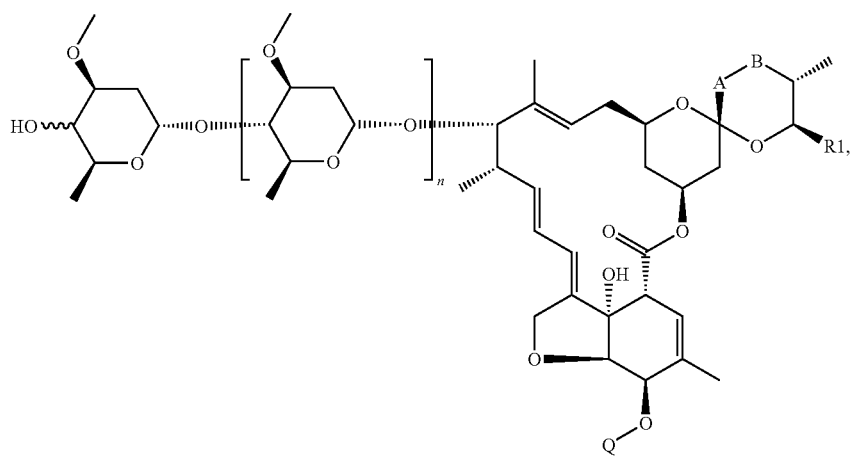

wherein $R_1$, n and the grouping A-B are as defined above under group (1) for formula (I) and Q is a protecting group, and which is known or can be prepared by methods known per se, with a compound of formula

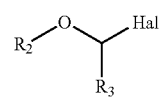

wherein $R_2$ and $R_3$ are as defined above for formula (I) and Hal is a halogen atom, preferably bromine or iodine, and which is known or can be prepared by known methods, to form a compound of formula

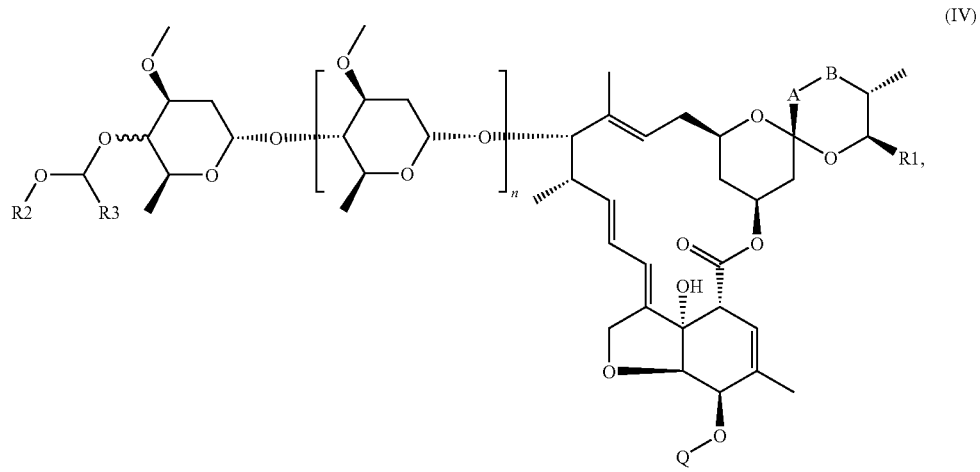

wherein Q, R₁, R₂ and R₃ are as defined for formula (II); and (B) removing the protecting group Q of the compound of formula (IV) so obtained.

The invention further relates to a process for the preparation of the compounds of formula (I) as defined above under group (1), wherein R₃ is —CH₂R₇

(C) reacting a compound of formula (II) with a compound of formula

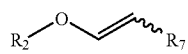
(V)

wherein R₂ is as defined for formula (I) and R₇ is H, $C_1$-$C_{11}$-alkyl or $C_1$-$C_{11}$-halogenalkyl; or R₂ are R₇ together are a three- to six-membered alkylen- or a four- to six-membered alkenylen, wherein one CH₂-group is optionally replaced by a group selected from C(=O), —C=S, O, S, —NR₅, —OC(=O)O—, —OC(=O)S—, —OC(=O)NR₅—, —C(=O)O—, —C(=O)S—, —C(=O)NR₅—, —NR₅C(=O)S— and —NR₅CONR₅—, and wherein alkenylen is optionally substituted with one or two substituents which are selected form the group consisting of $C_1$-$C_4$-alkyl, $C_1$-$C_4$-alkoxy and $C_1$-$C_4$-halogenalkyl, and wherein the said substituents are independent of each other;

(D) In particular, compounds of the formula (I), wherein R₃ is CH₂Hal and Hal is a halogen can be prepared by deprotection of compounds of the formula (IV), wherein R₃ is CH₂Hal. The latter can be prepared by haloacetalization of compounds of the formula

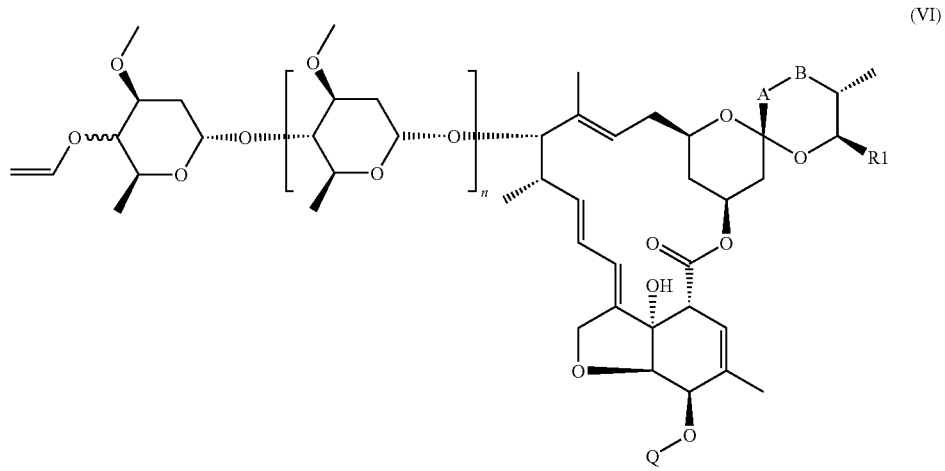

Compounds of the formula (VI) can be prepared by vinylation of compounds of the formula (II).

Compounds of the formula (IV), wherein $R_3$ is $CH_2Hal$ can in particular be used to prepare other compounds of the formula (IV), wherein $R_3$ is $CH_2R_8$, wherein $R_8$ is CN, $NR_4R_6$, —NHC(=O)$R_4$, $NHNH_2$, $NHNHR_4$, $NR_4NR_4R_6$, $OR_4$ or $SR_4$.

Compounds of the formula (IV) are preferred compounds for the preparation of compounds of the formula (I).

Furthermore compounds of formula (I) bearing a functional group in its free or protected form can be used as starting materials for the preparation of further compounds of formula (I). For such manipulations methods known to the person skilled in the art can be applied.

For example a compound of formula (I) wherein $R_2$ is $CH_2CH_2C(=O)CH_3$ can be converted to a compound of formula (I) wherein $R_2$ is $CH_2CH_2OH$. Further standard reactions can deliver compounds of formula (I) wherein $R_2$ is $CH_2CH_2OCH_2O$-Alkyl, $CH_2CH_2C(=O)R_4$, $CH_2CH_2C(=O)ZR_4$ and $CH_2CH_2N_3$. A compound of formula (I) wherein $R_2$ is $CH_2CH_2N_3$ can be converted to a compound of formula (I) wherein $R_2$ is $CH_2CH_2NH_2$. Treatment of such a compound of formula (I) with Hal-C(=O)$R_4$ or Hal-C(=O)$ZR_4$ gives compounds of formula (I) wherein $R_2$ is $CH_2CH_2NHC(=O)R_4$ and $CH_2CH_2NHC(=O)ZR_4$ respectively The reactions described hereinbefore and hereinafter are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel under pressure, under an inert gas atmosphere and/or under anhydrous conditions. Especially advantageous reaction conditions can be found in the Examples.

The reaction time is not critical; however a reaction time of from approximately 0.1 to approximately 72 hours, especially from approximately 0.5 to approximately 24 hours, is preferred.

The product is isolated by customary methods, for example by means of filtration, crystallisation, distillation or chromatography, or any suitable combination of such methods.

The starting materials mentioned hereinbefore and hereinafter that are used for the preparation of the compounds of formula (I) and, where applicable, their tautomers are known or can be prepared by methods known per se, e.g. as indicated below.

Process Variant (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile; sulfoxides, such as dimethyl sulfoxide; or mixtures of the mentioned solvents. Preference is given to amides, such as dimethylformamide and dimethylacetamide, especially dimethylacetamide.

Protecting groups Q in the compounds of formulae (II) and (IV) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

The reactions are advantageously carried out in a temperature range of from approximately −70° C. to 50° C., preferably at from −10° C. to 25° C.

Examples P.1 and P2 provide in more detail the reaction conditions.

Process Variant (B):

Examples of solvents and diluents are the same as those mentioned under Process variant A. In addition, alcohols, such as methanol, ethanol or 2-propanol, and water are suitable.

The reactions are advantageously carried out in a temperature range of approximately from −70° C. to 100° C., preferably at from −10° C. to 25° C.

There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

Especially preferred conditions for the reaction are described in Example P.1, P2, P3, P4 and P5.

Process Variant (C):

Examples of solvents and diluents are the same as those mentioned under Process variant A.

The reactions are advantageously carried out in a temperature range of approximately from −70° C. to 100° C., preferably at from −10° C. to 55° C.

The reaction is preferably performed in the presence of an acid or Lewis acid. Typical acids and Lewis acids are especially mineral acids, e.g. sulfuric acid, a phosphoric acid or a hydrohalic acid, especially hydrochloric acid, methanesulfonic acid, e.g. halo-substituted, $C_1$-$C_4$alkanecarboxylic acid, for example acetic acid, a saturated or unsaturated dicarboxylic acid, for example oxalic acid, malonic acid, maleic acid, fumaric acid or phthalic acid, a hydroxycarboxylic acid, for example ascorbic acid, lactic acid, malic acid, tartaric acid or citric acid, or benzoic acid, or $BF_3*OEt_2$.

Process Variant (D):

Examples of solvents and diluents are the same as those mentioned under Process variant A.

The reactions are advantageously carried out in a temperature range of approximately from −70° C. to 150° C., preferably at from −20° C. to 120° C.

Preferred reaction conditions for the haloacetalization and the vinylation are as such as described in the literature known to a person skilled in the art.

The compounds of formula (I) may be in the form of one of the possible isomers or in the form of a mixture thereof, in the form of pure isomers or in the form of an isomeric mixture, i.e. in the form of a diastereomeric mixture; the invention relates both to the pure isomers and to the diastereomeric mixtures and is to be interpreted accordingly hereinabove and hereinbelow, even if stereochemical details are not mentioned specifically in every case.

The diastereomeric mixtures can be resolved into the pure isomers by known methods, for example by recrystallisation from a solvent, by chromatography, for example high pressure liquid chromatography (HPLC) on acetylcellulose, with the aid of suitable micro-organisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its diastereomers, or, especially, is formed under the reaction conditions. For instance compounds of formula (I) bearing a functional group in its free or protected form can be used as starting materials for the preparation of further compounds of formula (I). For such manipulations methods known to the person skilled in the art can be applied.

In the processes of the present invention it is preferable to use those starting materials and intermediates which result in the compounds of formula (I) that are especially preferred.

The invention relates especially to the preparation processes described in the Examples.

The invention further relates to the compounds of formula (IV) and, where applicable, E/Z isomers, mixtures of E/Z isomers and/or tautomers, in each case in free form or in salt form.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Acarina, Diptera, Thysanoptera, Lepidoptera and Coleoptera. Very especially good control is possible of the following pests:

*Abagrotis* spp., *Abraxas* spp., *Acantholeucania* spp., *Acanthoplusia* spp., *Acarus* spp., *Acarus siro*, *Aceria* spp., *Aceria sheldoni*, *Acleris* spp., *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* ssp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacamptodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* ssp., *Anthonomus grandis*, *Anticarsia* spp., *Anticarsia gemmatalis*, *Aonidiella* spp., *Apamea* spp., *Aphania* spp., *Aphelia* spp., *Aphididae*, *Aphis* spp., *Apotomis* spp., *Aproaerema* spp., *Archippus* spp., *Archips* spp., *Acromyrmex*, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp., *Asthenoptycha* spp., *Aterpia* spp., *Athetis* spp., *Atomaria* spp., *Atomaria linearis*, *Atta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp., *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp., *Ceratophyllus* spp., *Ceroplaster* spp., *Chaetocnema* spp., *Chaetocnema tibialis*, *Chamaesphecia* spp., *Charanvca* spp., *Cheimophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aonidium*, *Chrysoteuchia* spp., *Cilix* spp., *Cimex* spp., *Clysia* spp., *Clysia ambiguella*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Cornutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Ctenocephalides* spp., *Cucullia* spp., *Curculio* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., *Dichomeris* spp., *Dichrocrocis* spp., *Dichrorampha* spp., *Dicycla* spp., *Dioryctria* spp., *Diparopsis* spp., *Diparopsis castanea*, *Dipleurina* spp., *Diprion* spp., *Diprionidae*, *Discestra* spp., *Distantiella* spp., *Distantiella theobroma*, *Ditula* spp., *Diurnea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., *mpoasca* spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Eplema* spp., *Epipsestis* spp., *Epirrhoe* spp., *Episimus* spp., *Epitymbia* spp., *Epilachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosma* spp., *Euehlaena* spp., *Euelidia* spp., *Eueosma* spp., *Euchistus* spp., *Eucosmomorpha* spp., *Eudonia* spp., *Eufidonia* spp., *Euhyponomeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp., *Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Frankliniella* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gypsonoma* spp., *Hada* spp., *Haematopinus* spp., *Halisidota* spp., *Harpipteryx* spp., *Harrisina* spp., *Hedya* spp., *Helicoverpa* spp., *Heliophobus* spp., *Heliothis* spp., *Hellula* spp., *Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homoglaea* spp., *Homohadena* spp., *Homona* spp., *Homonopsis* spp., *Hoplocampa* spp., *Hoplodrina* spp., *Hoshinoa* spp., *Hxalomma* spp., *Hydraecia* spp., *Hydriomena* spp., *Hyles* spp., *Hyloicus* spp., *Hypagyrtis* spp., *Hypatima* spp., *Hyphantria* spp., *Hyphantria cunea*, *Hypocala* spp., *Hypocoena* spp., *Hypodema* spp., *Hyppobosca* spp., *Hypsipyla* spp., *Hyssia* spp., *Hysterosia* spp., *Idaea* spp., *Idia* spp., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella*, *Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata*, *Leptocorisa* spp., *Leptostales* spp., *Lecanium* spp., *Lecanium comi*, *Lepidosaphes* spp., *Lepisma* spp., *Lepisma saccharina*, *Lesmone* spp., *Leucania* spp., *Leucinodes* spp., *Leucophaea* spp., *Leucophaea maderae*, *Leucoptera* spp., *Leucoptera scitella*, *Linognathus* spp., *Liposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana*, *Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp., *Macrauzata* spp., *Macronoctua* spp., *Macrosiphus* spp., *Malacosoma* spp., *Maliarpha* spp., *Mamestra* spp., *Mamestra brassicae*, *Manduca* spp., *Manduca sexta*, *Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis*, *Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp., *Olethreutes* spp., *Oligia* spp., *Olindia* spp., *Olygonychus* spp., *Olygonychus gallinae*, *Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit*, *Osminia* spp., *Ostrinia* spp., *Ostrinia nubilalis*, *Otiorhynchus* spp., *Ourapteryx* spp., *Pachetra* spp., *Pachysphinx* spp., *Pagyda* spp., *Paleacrita* spp., *Paliga* spp., *Palthis* spp., *Pammene* spp., *Pandemis* spp., *Panemeria* spp., *Panolis* spp., *Panolis flammea*, *Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromeme* spp., *Pectinophora* spp., *Pectinophora gossypiella*, *Pediculus* spp., *Pegomyia* spp., *Pegomyia hyoscyami*, *Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella*, *Phyllocnistis* spp., *Phyllocoptruta* spp., *Phyllocoptruta oleivora*, *Phyllonorycter* spp., *Phyllophila* spp., *Phylloxera* spp., *Pieris* spp., *Pieris rapae*, *Piesma* spp., *Planococus* spp., *Planotortrix* spp., *Platyedra* spp., *Platynota* spp., *Platyptilia* spp., *Platysenta* spp., *Plodia* spp., *Plusia* spp., *Plutella* spp., *Plutella xylostella*, *Podosesia* spp., *Polia* spp., *Popillia* spp., *Polymixis* spp., *Polyphagotarsonemus* spp., *Polyphagotarsonemus latus*, *Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylla* spp., *Psylliodes* spp., *Pterophorus* spp., *Ptycholoma* spp., *Pulvinaria* spp., Pulvinaria aethiopica, *Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp, Rhagoletis pomonella, *Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrina* spp., *Rynchaglaea* spp., *Sabulodes* spp., *Sahlbergella* spp., *Sahlbergella singularis*, *Saissetia* spp., *Samia* spp., *Sannina* spp., *Sanninoidea* spp., *Saphoideus* spp., *Sarcoptes* spp., *Sathrobrota* spp., *Scarabeidae*, *Sceliodes* spp., *Schinia* spp., *Schistocerca* spp., *Schizaphis* spp., *Schizura* spp., *Schreckensteinia* spp., *Sciara* spp., *Scirpophaga* spp., *Scirthrips auranti*, *Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia* spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis*, *Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Teleiodes* spp., *Telorta* spp., *Tenebrio* spp., *Tephrina* spp., *Teratoglaea* spp., *Terricula* spp., *Tethea* spp., *Tetranychus* spp., *Thalpophila* spp., *Thaumetopoea* spp., *Thiodia* spp., *Thrips* spp., *Thrips* palmi, *Thrips tabaci*, *Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum*, *Triatoma* spp., *Triaxomera* spp., *Tribolium* spp., *Tricodectes* spp., *Trichoplusia* spp., *Trichoplusia ni*, *Trichoptilus* spp., *Trioza* spp., Trioza erytreae, *Triphaenia* spp., *Triphosa* spp., *Trogoderma* spp., *Tyria* spp., *Udea* spp., *Unaspis* spp., *Unaspis* citri, *Utetheisa* spp., *Valeriodes* spp., *Vespa* spp., *Vespamima* spp., *Vitacea* spp., *Vitula* spp., *Witlesia* spp., *Xanthia* spp., *Xanthorhoe* spp., *Xanthotype* spp., *Xenomicta* spp., *Xenopsylla* spp., *Xenopsylla* cheopsis, *Xestia* spp., *Xylena* spp., *Xylomyges* spp., *Xyrosaris* spp., *Yponomeuta* spp., *Ypsolopha* spp., *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. Radopholus similis; *Pratylenchus*, e.g. *Pratylenchus neglectans* and *Pratylenchus penetrans*; *Tylenchulus*, e.g. *Tylenchulus semipenetrans*; *Longidorus*, *Trichodorus*, *Xiphinema*, *Ditylenchus*, *Apheenchoides* and *Anguina*; especially *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; clothianidin; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; pyridalyl; fenazaquin; pyriproxyfen; pyrimidifen; nitenpyram; acetamiprid; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; abamectin, chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam;

mesulfenphos; metaldehyde; metolcarb; milbemectin; moxidectin; naled; NC 184; nithiazine; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiamethoxam; thiodicarb; thiofanox; thionazin; thuringiensin; tralomethrin; triarathene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium* anisopliae.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants which are customary in formulation technology and are suitable according to the invention are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypolyethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of—at least—one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions comprise ingredients within the following ranges (%=percent by weight):

Emulsifiable Concentrates:

| active ingredient: | 1 to 90%, preferably 5 to 20% |
| --- | --- |
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
| --- | --- |
| solid carrier: | 99.9 to 90%, preferably 99.9 to 99% |

Suspension Concentrates:

| active ingredient: | 5 to 75%, preferably 10 to 50% |
| --- | --- |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| --- | --- |
| surfactant: | 0.5 to 20%, preferably 1 to 15% |
| solid carrier: | 5 to 99%, preferably 15 to 98% |

Granules:

| active ingredient: | 0.5 to 30%, preferably 3 to 15% |
| --- | --- |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha; more especially 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

The following Examples serve to illustrate the invention. They do not limit the invention. Temperatures are in degrees Celsius; mixing ratios of solvents are given in parts by volume. In the data relating to NMR spectra, DMSO denotes dimethyl sulfoxide, s denotes singlet, t denotes triplet, d denotes doublet, q denotes quartet and m denotes multiplet.

PREPARATION EXAMPLES

In the following Examples, the preparation of avermectin B1 derivatives (mixtures of avermectin B1a and B1b derivative) is described. The B1b derivative generally represents about only from 5 to 10% by weight of the mixtures and, for that reason, usually only the bands of the B1a derivative can be detected in the NMR spectrum.

Since the compounds are in most cases in the form of mixtures of the avermectin B1a and B1b derivative, characterisation by means of the customary physical data such as melting point or refractive index is of little use. For that reason, the compounds are characterised by means of NMR spectroscopy following purification by chromatography, or by reference to the retention times determined in analysis by means of HPLC (high-resolution liquid chromatography). The term "B1a" in the physical data on the Preparation Examples refers to the main component, wherein $R_1$ is sec-butyl. "B1b" represents the secondary component, wherein $R_1$ is isopropyl. In the case of the compounds for which a retention time is given only for the B1a derivative, it is not possible to determine the retention time for the B1b component owing to the small proportion of B1b derivative. Allocation of the correct structures of the B1a and B1b components is carried out by mass spectrometry.

| -continued | | | |
|---|---|---|---|
| 17.1 | 80 | 20 | 500 |
| 22 | 80 | 20 | 500 |
| column: | YMC-Pack ODS-AQ | | |
| column length: | 125 mm | | |
| column internal diameter: | 2 mm | | |
| temperature: | 40° C. | | |

The YMC-Pack ODS-AQ column used for chromatography of the compounds is produced by YMC, Alte Raesfelderstrasse 6, 46514 Schermbeck, Germany.

The abbreviations used in the physical data information have the following meanings:

s: singlet, MHz: megahertz, brs: broad singlet; t: triplet; m: multiplet; d: doublet; J: coupling constant; bd: broad doublet; LCMS: liquid chromatography mass spectrometry; $t_{RT}$: retention time in minutes; M+H: mass peak plus H; M+Na: mass peak plus Na. TBDMS in the Examples represents the radical —Si(CH$_3$)$_2$(tert-butyl). Mixing ratios of solvents are given in parts by volume. "Ether" is understood to mean diethyl ether.

Example P.1

4"-O-benzyloxymethyl-Avermectin B$_1$

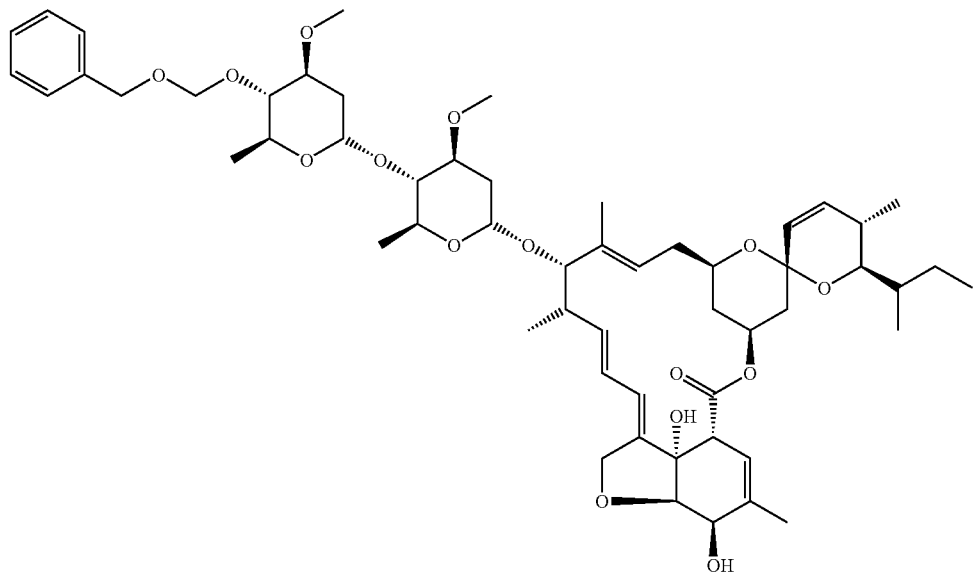

The following method is used for the HPLC analysis:

| HPLC gradient conditions | | | |
|---|---|---|---|
| solvent A: | 0.01% trifluoroacetic acid in H$_2$O | | |
| solvent B: | 0.01% trifluoroacetic acid in CH$_3$CN | | |
| time [min] | A [%] | B [%] | flow rate [µl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |

Step A: To a solution of 0.5 g of 5-OTBDMS-Avermectin B$_1$ and 0.26 g of N,N-diisopropylethylamine in 10 ml dichloromethane at 0° C. is added 276 mg of benzyloxymethyl chloride. The mixture is stirred at 35° C. for 12 hours. The reaction mixture is cooled to room temperature, poured into water, extracted with ethyl acetate, dried over Na$_2$SO$_4$, and concentrated in vacuo, providing crude 5-OTBDMS-4"-O-benzyloxymethyl-Avermectin B$_1$ which was used directly as follows:

Step B: To a solution of 5-OTBDMS-4"-O-benzyloxymethyl-Avermectin B$_1$ (obtained in step A) in 10 ml tetrahydrofuran is added 2.2 ml of a HF-pyridine solution (consisting of 25 g 70% HF-Pyridin, 27.5 ml tetrahydrofuran and 12.5 ml pyridine), and the mixture is stirred at room temperature for 12 hours, poured into water, extracted with ethyl acetate; the organic phase is washed with saturated sodium bicarbonate, dried over sodium sulfate, and concentrated in vacuo. The residue is purified by preparative HPLC to afford 4"-O-benzyloxymethyl-Avermectin B$_1$. LCMS: B$_{1a}$: t$_{RT}$: 12.16 min., 1015 (M+Na).

Example P.2

4"-epi-O-(2-methoxyethoxymethyl)-Avermectin B$_1$

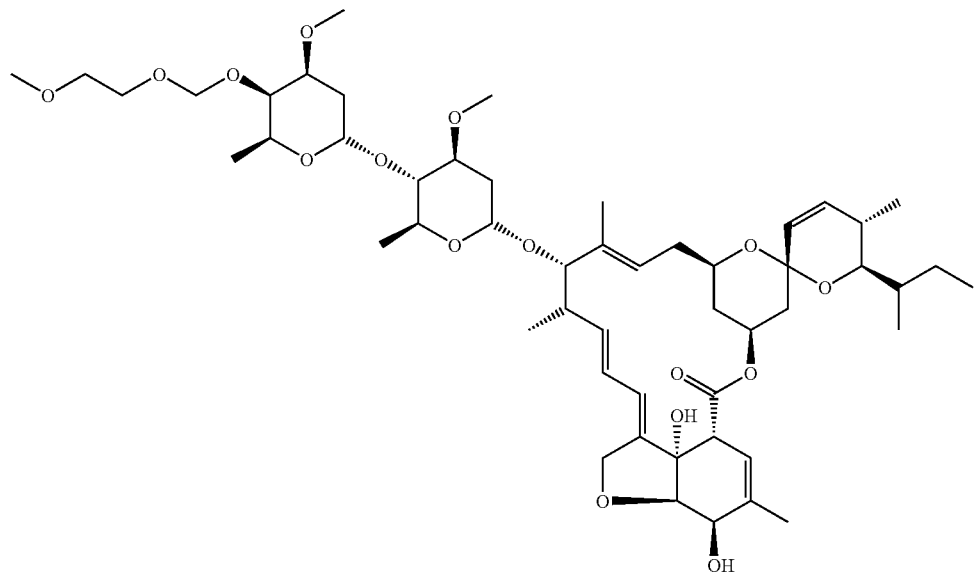

Step A: To a solution of 0.3 g of 5-OTBDMS-4"-epi-Avermectin B$_1$ and 0.31 g of N,N-diisopropylethylamine in 5 ml dichloromethane at 0° C. is added 0.21 ml of 2-methoxyethoxymethyl chloride. The mixture is stirred at reflux for 6 hours. The reaction mixture is cooled to room temperature poured into water, extracted with ethyl acetate, dried over Na$_2$SO$_4$, and concentrated in vacuo, providing crude 5-OTBDMS-4"-epi-O-(2-methoxy-ethoxymethyl)-Avermectin B$_1$ which is used directly as follows:

Step B: To a solution of 5-OTBDMS-4"-epi-O-(2-methoxyethoxymethyl)-Avermectin B$_1$ in 10 ml tetrahydrofuran is added 3.5 ml of a HF-pyridine solution (consisting of 25 g 70% HF-Pyridin, 27.5 ml tetrahydrofuran and 12.5 ml pyridine), and the mixture is stirred at 50° C. for 2.5 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate 1/1), to afford 4"-epi-O-(2-methoxyethoxymethyl)-Avermectin B$_1$. LCMS: B$_{1a}$: t$_{RT}$: 9.37 min., 983.5 (M+Na), 961.6 (M+H); B$_{1a}$: t$_{RT}$: 8.65 min., 969.5 (M+Na).

Example P.3

4'-O-Butoxymethyl-Avermectin B$_1$ monosaccharide

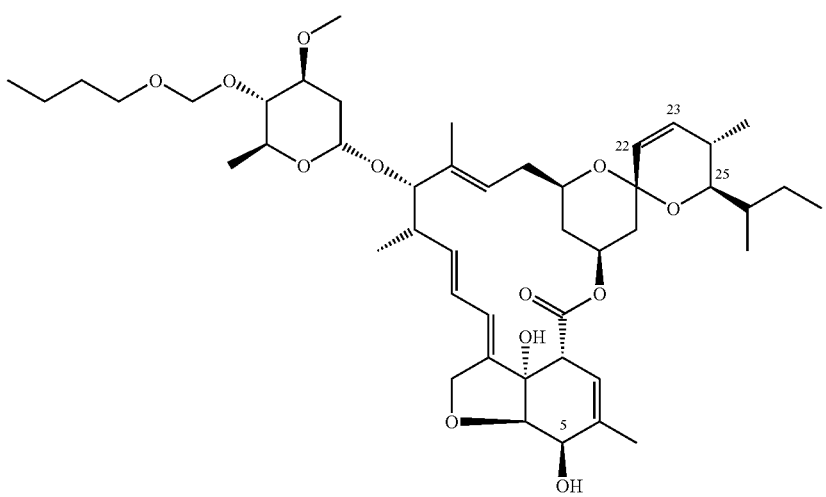

Step A: To a solution of 5-OTBDMS-Avermectin $B_1$ monosaccharide (420 mg) and N,N-diisopropylethylamine (0.4 ml) in dichloromethane (5 ml) at room temperature is added chloromethyl n-butyl ether (220 mg). The mixture is stirred at 35° C. for 24 hours. The reaction mixture is poured into brine, extracted with ethyl acetate, dried over $Na_2SO_4$, and concentrated in vacuo. The residue is purified by flash chromatography (silica gel, hexane/ethyl acetate 4/1) providing 5-OTBDMS-4'-O-butoxymethyl-avermectin $B_1$ monosaccharide which is characterized by its mass and NMR spectra.

Step B: To a solution of 5-OTBDMS-4'-O-butoxymethyl-avermectin $B_1$ monosaccharide (200 mg) in methanol (5 ml) at 0° C. is added methanesulphonic acid (0.02 ml). The reaction mixture is stirred for 1 hour and poured into saturated sodium bicarbonate, extracted with ethyl acetate, dried over $Mg_2SO_4$, and concentrated in vacuo. Flash chromatography (silica gel, hexane/ethyl acetate 3/0) affords 4'-O-butoxymethyl-avermectin $B_1$ monosaccharide.

4'-O-Butoxymethyl-Avermectin $B_1$ monosaccharide: $B_{1a}$ $C_{46}H_{70}O_{12}$, MW: 814.5. LCMS: $t_{RT}$: 11.4 minutes, 837.3 (M+Na); 1H NMR (300 MHz, $CDCl_3$) selected data, δH (ppm): 3.15 (t, J=8.5 Hz, 1H, CH-4'), 3.28 (m, 1H, CH-2), 3.44 (s, 3H, $OCH_3$). $B_{1b}$ $C_{45}H_{68}O_{12}$, MW: 800.5. LCMS: $t_{RT}$: 10.6 823.5 (M+Na);

Example P.4

4'-O-(1-Acetoxy-ethoxy)methyl-Avermectin $B_1$ monosaccharide

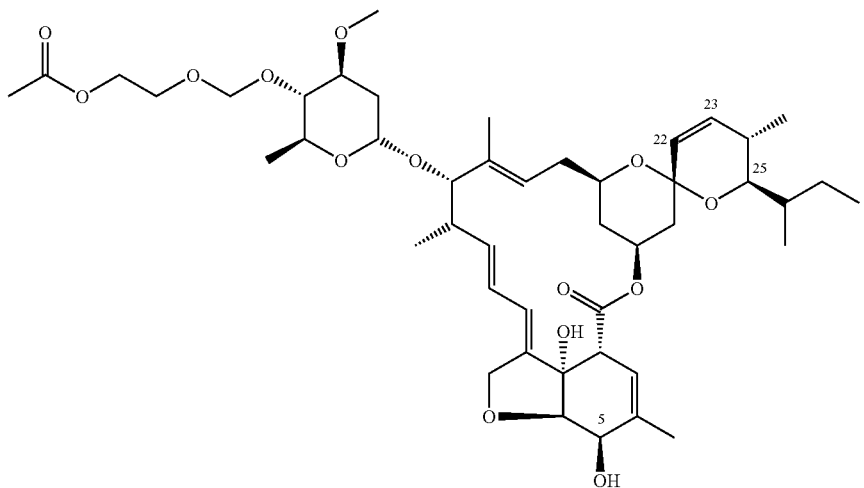

Step A: To a solution of 5-OTBDMS-Avermectin $B_1$ monosaccharide (422 mg) and N,N-diisopropylethylamine (0.9 ml) in dichloromethane (5 ml) at room temperature is added 1-acetoxy-2-chloromethoxyethane (610 mg). The mixture is stirred at 45° C. for 32 hours. The reaction mixture is poured into brine, extracted with ethyl acetate, dried over $MgSO_4$, and concentrated in vacuo. The residue is purified by flash chromatography (silica gel, hexane/ethyl acetate 4/1) providing 5-OTBDMS-4'-O-(1-acetoxy-ethoxy)methyl-avermectin $B_1$ monosaccharide which is characterized by its mass and NMR spectra.

Step B: To a solution of 5-OTBDMS-4'-O-(1-acetoxy-ethoxy)methyl-avermectin $B_1$ monosaccharide (384 mg) in Tetrahydrofuran (5 ml) is added pyridine (0.2 ml) and 0.2 ml of a 70% HF-pyridine solution. The mixture is stirred for 18 hours at room temperature, poured into aqueous $NaHCO_3$ (50%), extracted with ethyl acetate, dried over $MgSO_4$, and concentrated in vacuo. Flash chromatography (silica gel, hexane/ethyl acetate 1/1) affords 4'-O-(1-acetoxy-ethoxy)methyl-avermectin $B_1$ monosaccharide which is characterized by its mass and NMR spectra.

4'-O-(1-Acetoxy-ethoxy)methyl-avermectin $B_1$ monosaccharide: $B_{1a}$ $C_{48}H_{68}O_{14}$, MW: 844.5. LCMS: $t_{RT}$: 8.49 minutes, 867.5 (M+Na); $B_{1b}$ $C_{45}H_{66}O_{12}$, MW: 830.5. LCMS: $t_{RT}$: 7.82 minutes, 853.5 (M+Na).

Example P.5

4'-O-(1-hydroxy-ethoxy)methyl-Avermectin B$_1$ monosaccharide

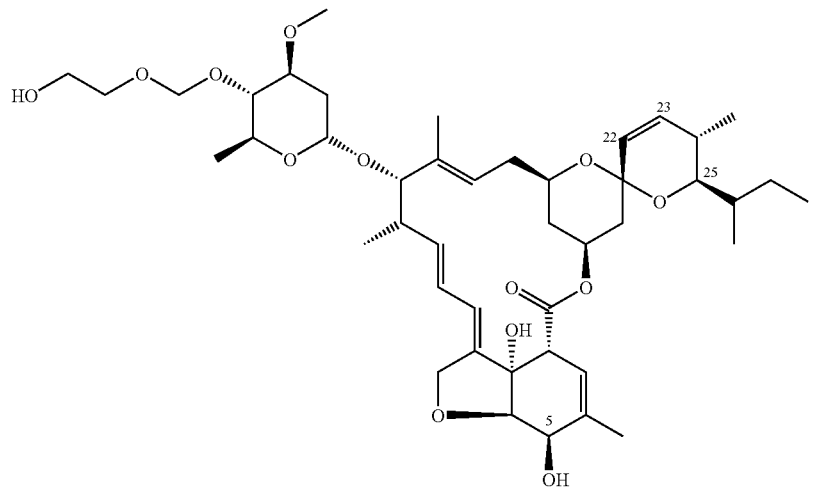

Step A: To a methanolic solution (10 ml) of 5-OTBDMS-4'-O-(1-acetoxy-ethoxy)methyl-avermectin B$_1$ monosaccharide (410 mg) cooled to 0° C. is added ammonium hydroxide (2 ml, 25% in H$_2$O). The mixture is stirred at room temperature for 4 hours at room temperature and then concentrated in vacuo. Flash chromatography (silica gel, hexane/ethyl acetate 1/1) affords 4'-O-(1-hydroxy-ethoxy)methyl-avermectin B$_1$ monosaccharide which is characterized by its mass and NMR spectra.

Step B: To a solution of 5-OTBDMS-4'-O-(1-hydroxy-ethoxy)methyl-avermectin B$_1$ monosaccharide (140 mg) in Tetrahydrofuran (2 ml) is added pyridine (80 µl) and 70% HF-pyridine solution (80 µl). The mixture is stirred for 5 d at room temperature, poured into aqueous NaHCO$_3$ (50%), extracted with ethyl acetate, dried over MgSO$_4$, and concentrated in vacuo. Flash chromatography (silica gel, hexane/ethyl acetate 3/7) affords 4'-O-(1-hydroxy-ethoxy)methyl-avermectin B$_1$ monosaccharide which is characterized by its mass and NMR spectra.

4'-O-(1-hydroxy-ethoxy)methyl-avermectin B$_{1a}$ monosaccharide: B$_{1a}$ C$_{44}$H$_{66}$O$_{13}$, MW: 802.5. LCMS: t$_{RT}$: 6.99 minutes, 825.4 (M+Na); B$_{1b}$ C$_{43}$H$_{64}$O$_{13}$, MW: 788.4. LCMS: t$_{RT}$: 6.35 minutes, 811.4 (M+Na).

Example P.6

4'-O-(1-Methoxymethoxy-ethoxy)methyl-Avermectin B$_1$ mono-saccharide

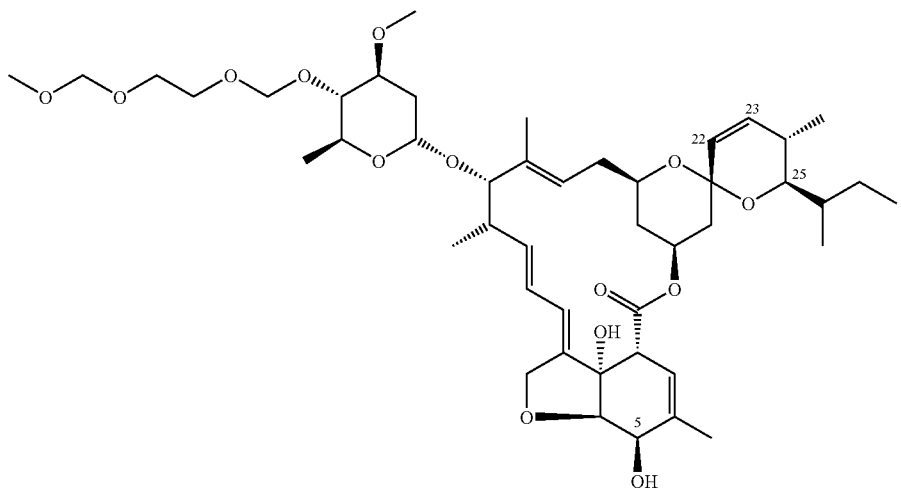

Step A: To a solution 5-OTBDMS-4'-O-(1-hydroxyethoxy)methyl-avermectin $B_1$ monosaccharide (138 mg) and N,N-diisopropylethylamine (90 μl) in dichloromethane (5 ml) at room temperature is added chloromethyl methyl ether (29 μl). The mixture is stirred at 35° C. for 20 hours. The reaction mixture is poured into water, extracted with dichloromethane, dried over $MgSO_4$ and concentrated in vacuo. The residue is purified by flash chromatography (silica gel, hexane/ethyl acetate 7/3) providing 5-OTBDMS-4'-O-(1-methoxymethoxy-ethoxy)methyl-Avermectin $B_1$ monosaccharide, which is characterized by its mass and NMR spectra.

Step B: To a solution of 5-OTBDMS-4'-O-(1-methoxymethoxy-ethoxy)methyl-avermectin $B_1$ mono-saccharide (100 mg) in Tetrahydrofuran (1.5 ml) is added pyridine (50 μl) and 70% HF-pyridine solution (50 μl). The mixture is stirred for 48 hours at room temperature, poured into saturated aqueous $NaHCO_3$, extracted with ethyl acetate, dried over $MgSO_4$ and concentrated in vacua. Flash chromatography (silica gel, hexane/ethyl acetate 1/1) affords 4'-O-(1-methoxymethoxy-ethoxy)methyl-avermectin $B_1$ mono-saccharide which is characterized by its mass and NMR spectra.

4'-O-(1-Methoxymethoxy-ethoxy)methyl-avermectin $B_1$ monosaccharide: $B_{1a}$ $C_{46}H_{70}O_{14}$, MW: 846.5. LCMS: $t_{RT}$: 8.73 minutes, 869.4 (M+Na); $B_{1b}$ $C_{45}H_{68}O_{14}$, MW: 832.5. LCMS: $t_{RT}$: 7.89 minutes, 855.4 (M+Na).

Example P.7

4'-O-(1-azido-ethoxy)methyl-Avermectin $B_1$ monosaccharide

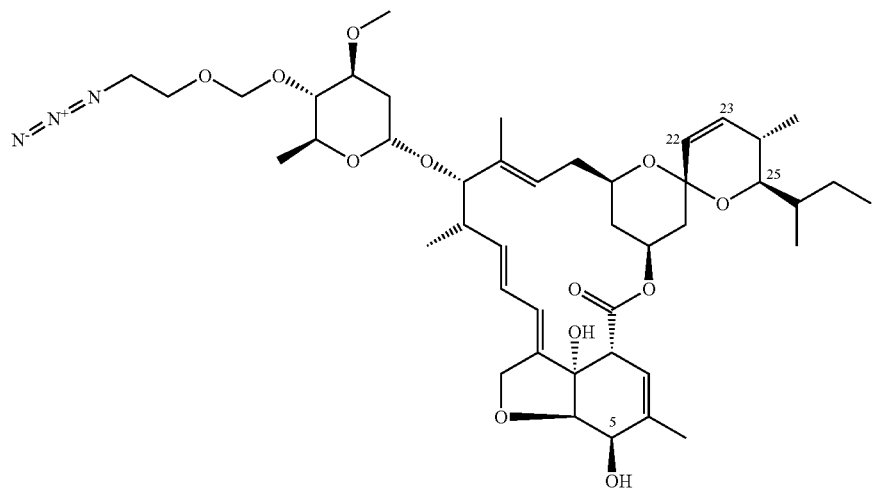

Step A: To a solution 5-OTBDMS-4'-O-(1-hydroxyethoxy)methyl-avermectin $B_1$ monosaccharide (642 mg) in N,N-dimethylacetamide (7 ml) cooled to 0° C. room temperature is added triphenylphosphine (551 mg) and tetrabromomethane (696 mg). The mixture is stirred for 0.5 hours after which time sodium azide (228 mg) is added. The reaction mixture is stirred at 40° C. for 1 hours and then poured into water, extracted with ethyl acetate, dried over $MgSO_4$ and concentrated in vacuo. The residue is purified by flash chromatography (silica gel, hexane/ethyl acetate 5/1) providing 5-OTBDMS-4'-O-(1-azido-ethoxy)methyl-Avermectin $B_1$ monosaccharide which is characterized by its mass and NMR spectra.

Step B: To a solution of 5-OTBDMS-4'-O-(1-azido-ethoxy)methyl-Avermectin $B_1$ monosaccharide (98 mg) in tetrahydrofuran (2.0 ml) is added pyridine (50 μl) and 70% HF-pyridine solution (50 μl). The mixture is stirred for 48 hours at room temperature, poured into saturated aqueous $NaHCO_3$, extracted with ethyl acetate, dried over $MgSO_4$ and concentrated in vacuo. Flash chromatography (silica gel, hexane/ethyl acetate 1/1) affords 4'-O-(1-azido-ethoxy)methyl-avermectin $B_1$ monosaccharide which is characterized by its mass and NMR spectra.

4'-O-(1-Azido-ethoxy)methyl-avermectin $B_1$ monosaccharide: $B_{1a}$ $C_{44}H_{11}N_3O_{12}$, MW: 827.5. LCMS: $t_{RT}$: 9.76 minutes, 850.5 (M+Na); $B_{1b}$ $C_{43}H_{63}N_3O_{12}$, MW: 813.4 LCMS: $t_{RT}$: 9.01 minutes, 836.4 (M+Na).

Example P.8

4'-O-(1-amino-ethoxy)methyl-Avermectin $B_1$ monosaccharide

Step A: To a solution of 4'-O-(1-azido-ethoxy)methyl-avermectin $B_1$ monosaccharide is added trimethylphosphine (150 µl, 1.0 M in tetrahydrofuran) and water (30 µl). The reaction mixture is stirred at room temperature for 48 hours and then poured into water, extracted with ethyl acetate, dried over $MgSO_4$ and concentrated in vacuo. The residue is purified by flash chromatography (silica gel, hexane/ethyl acetate 5/1) providing 4'-O-(1-aminoethoxy)methyl-Avermectin $B_1$ monosaccharide which is characterized by its mass and NMR spectra.

4'-O-(1-Amino-ethoxy)methyl-avermectin $B_1$ monosaccharide: $B_{1a}$ $C_{44}H_{87}NO_{12}$, MW: 801.5. LCMS: $t_{RT}$: 4.11 minutes, 802.5 (M+Na).

Example P.9

4'-O-(1-bromomethyl-1-methoxy)methyl-Avermectin $B_1$ monosaccharide

Step A: A mixture of 5-OTBDMS-Avermectin $B_1$ monosaccharide (1.0 g), mercury acetate (190 mg) and ethyl vinyl ether (10 ml) is refluxed for 8 h. The reaction mixture is poured into aqueous $Na_2CO_3$ and extracted with ethyl acetate. Drying over $Na_2SO_4$, and concentration in vacuo provides 5-OTBDMS-4'-O-vinyl-avermectin $B_1$ monosaccharide which is characterized by its mass and NMR spectra.

Step B: To a solution of 5-OTBDMS-4'-O-vinyl-avermectin $B_1$ monosaccharide (200 mg) in methanol is added N-bromosuccinimide (46 mg). After stirring at room temperature for 24 h the solvent is removed in vacuo providing 5-OTBDMS-4'-O-(1-bromomethyl-1-methoxy)methyl-Avermectin $B_1$ monosaccharide as a mixture of diastereoisomers which is characterized by its mass and NMR spectra.

5-OTBDMS-4'-O-(1-bromomethyl-1-methoxy)methyl-Avermectin $B_1$ monosaccharide: $B_{1a}$ $C_{50}H_{79}BrO_{12}Si$, MW: 978.5. LCMS: isomer 1: $t_{RT}$, 14.94 min., 979.5 (M+H); isomer 2: $t_{RT}$, 14.64 min., 1001.4 (M+Na).

Step C: To a solution of 5-OTBDMS-4'-O-(1-bromomethyl-1-methoxy)methyl-avermectin $B_1$ monosaccharide (200 mg) in THF (2.0 ml) is added pyridine (50 µl) and 70% HF-pyridine solution (100 µl). The mixture is stirred for 48 h at room temperature, poured into saturated aqueous $NaHCO_3$, extracted with ethyl acetate, dried over $MgSO_4$ and concentrated in vacuo. Flash chromatography (silica gel, hexane/ethyl acetate 1/1) affords 4'-O-(1-bromomethyl-1-methoxy)methyl-Avermectin $B_1$ monosaccharide which is characterized by its mass and NMR spectra.

4'-O-(1-Bromomethyl-1-methoxy)methyl-Avermectin $B_1$ monosaccharide: $B_{1a}$ $C_{44}H_{65}BrO_{12}$, MW: 864.4. LCMS: isomer 1 $t_{RT}$, 10.56 min., 865.4 (M+H); isomer 2: $t_{RT}$, 10.35 min., 865.4 (M+Na).

Example P.10

4'-epi-O-(Tetrahydro-pyran-2-yl)-avermectin $B_1$ monosaccharide of the formula

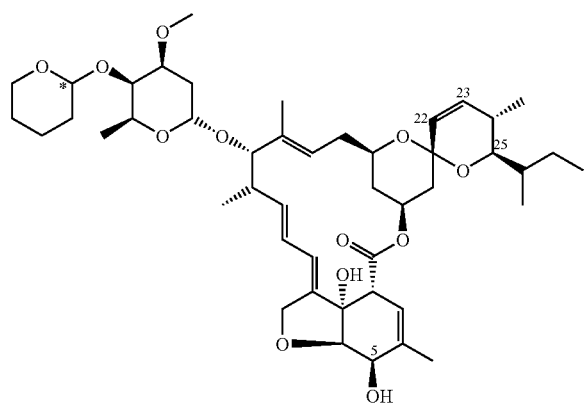

Step A: A mixture of 5-OTBDMS-4-epi-avermectin $B_1$ monosaccharide (500 mg), 3,4-Dihydro-2H-pyran (80.7 µl) and Pyridinium-(toluene-4-sulfonate) (14.9 mg) in 4 ml $CH_2Cl_2$ is stirred for 6 h at room temperature. The reaction mixture is diluted with 20 ml diethyl ether and washed with aqueous NaCl. Drying over $Na_2SO_4$, and concentration in vacuo provides the two possible isomers of 5-OTBDMS-4'-epi-O-(tetrahydro-pyran-2-yl)-avermectin $B_1$ monosaccharide which can be separated by flashchromatography (hexane-ethylacetate 4:1) and characterized by their mass and NMR spectra.

Step B': To a solution of the first isomer of 5-OTBDMS-4'-epi-O-(Tetrahydro-pyran-2-yl)-avermectin $B_1$ monosaccharide (148 mg) in THF (2.5 ml) is added pyridine (244 µl) and 70% HF-pyridine solution (83 µl). The mixture is stirred for 72 h at room temperature, poured into saturated aqueous $NaHCO_3$, extracted with ethyl acetate, dried over $Na_2SO_4$ and concentrated in vacuo. Preparative HPLC affords the first isomer of 4'-epi-O-(Tetrahydro-pyran-2-yl)-avermectin $B_1$ monosaccharide which is characterized by its mass and NMR spectra.

4'-epi-O-(Tetrahydro-pyran-2-yl)-avermectin $B_{1a}$ monosaccharide: $C_{46}H_{68}O_{12}$, MW: 812.5. LCMS: isomer 1 $t_{RT}$, 10.26 min., 813.5 (M+H); 835.5 (M+Na).

Step B'': To a solution of the second isomer of 5-OTBDMS-4'-epi-O-(tetrahydropyran-2-yl)-avermectin $B_1$ monosaccharide (46 mg) in THF (1 ml) is added pyridine (76 µl) and 70% HF-pyridine solution (26 µl). The mixture is stirred for 72 h at room temperature, poured into saturated aqueous $NaHCO_3$, extracted with ethyl acetate, dried over $Na_2SO_4$ and concentrated in vacuo. Preparative HPLC affords the second isomer of 4'-epi-O-(Tetrahydropyran-2-yl)-avermectin $B_1$ monosaccharide which is characterized by its mass and NMR spectra.

4'-epi-O-(Tetrahydro-pyran-2-yl)-avermectin $B_{1a}$ monosaccharide: $C_{46}H_{68}O_{12}$, MW: 812.5. LCMS: isomer 2 $t_{RT}$, 11.03 min., 813.5 (M+H); 835.5 (M+Na).

Example P.11

4'-O-([1,4]Dioxan-2-yl)-avermectin $B_1$ monosaccharide of the formula

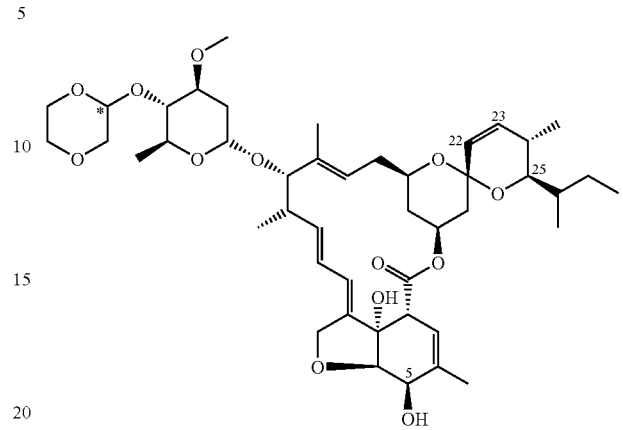

Step A: A mixture of 5-OTBDMS-4-avermectin $B_1$ monosaccharide (500 mg), 2-Phenylsulfanyl-[1,4]dioxane (163 mg) and molecular sieves (3 Å) in 8 ml $CH_2Cl_2$ is stirred for 2 h at room temperature. The reaction mixture is cooled to −30° C. and N-Iodosuccinimide (267 mg) and Trifluoromethansulfonic acid (5.1 µl) are added. After stirring for 75 min at that temperature, the reaction is quenched with Ethyldiisopropylamine (8.1 µl) diluted with 30 ml $CH_2Cl_2$ and washed with aqueous $Na_2S_2O_3$, aqueous $NaHCO_3$ and aqueous NaCl. Drying over $Na_2SO_4$, and concentration in vacuo provides 5-OTBDMS-4'-O-([1,4]Dioxan-2-yl)-avermectin $B_1$ monosaccharide which can be isolated by flashchromatography (hexane-ethylacetate 3:1) and characterized by its mass and NMR spectra.

Step B: To a solution of 5-OTBDMS-4'-O-([1,4]Dioxan-2-yl)-avermectin $B_1$ monosaccharide (29 mg) in THF (0.7 ml) is added HF-pyridine solution (175 µl). The mixture is stirred for 18 h at room temperature, poured into saturated aqueous $NaHCO_3$, extracted with ethyl acetate, dried over $Na_2SO_4$ and concentrated in vacuo. Flashchromatography (hexane-ethylacetate 1:1) affords 4'-O-([1,4]Dioxan-2-yl)-avermectin $B_1$ monosaccharide which is characterized by its mass and NMR spectra.

4'-O-([1,4]Dioxan-2-yl)-avermectin $B_{1a}$ monosaccharide: $C_{45}H_{66}O_{13}$, MW: 814.5. LCMS: $t_{RT}$, 10.07 min., 815.5 (M+H); 837.4 (M+Na); 832.5 (M+NH_4).

Example P.12

4'-O-(dihydro-pyran-3-one)-avermectin $B_1$ monosaccharide of the formula

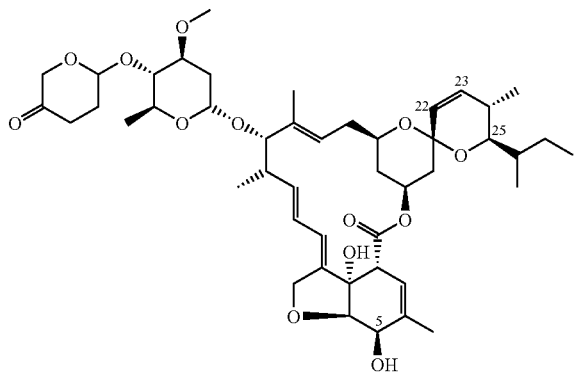

Step A: A solution of 5-OTBDMS-4-avermectin B₁ monosaccharide (7100 mg), Carbonic acid allyl ester 6-phenylsulfanyl-tetrahydro-pyran-3-yl ester (10240 mg and 2,6-di-tert-butylpyridine (1890 µl) in 40.0 ml of N-methylpyrrolidinone at room temperature is treated with N-iodosuccinimide (7650 mg) in 40 min. The reaction is quenched with a mixture of aqueous Na₂SO₃, aqueous K₂CO₃ and water. The aqueous phase is extracted with diethyl ether (3 times) and the organic phase is washed with water and aqueous NaCl successively. Drying over Na₂SO₄, and concentration in vacuo provides a mixture of three epimers of 4'-O-(3-allyloxycarbonyl-dihydro-pyran)-avermectin B₁ monosaccharide which can be isolated by flash chromatography (hexane-diethyl ether 1:0 to 0:1) and characterized by mass and NMR spectra. In the alternative they are kept as a mixture for the following step.

Step B: A solution of a mixture of 4'-O-(3-allyloxycarbonyl-dihydro-pyran)-avermectin B₁ monosaccharide (54300 mg), tetrakis(triphenylphosphine)-Palladium (2870 mg), triphenylphosphine (2580 mg), butylamine (7460 µL) and formic acid in 50.0 ml of tetrahydrofuran is stirred at room temperature for 4 h. The reaction is poured in a mixture of aqueous NaHCO₃ and ethyl acetate. The aqueous phase is extracted with ethyl acetate, dried over Na₂SO₄ and concentrated in vacuo. Flash chromatography (hexane-ethyl acetate 3:2) affords a mixture of epimers of 4'-O-(dihydro-pyran-3-ol)-avermectin B₁ monosaccharide which can be isolated by flash chromatography (hexane-diethyl ether 1:0 to 0:1) and characterized by mass and NMR spectra.

Step C: To a solution containing oxalyl chloride (1010 µL) in 30 mL of methylene chloride stirred at −75° C., is added DMSO (1390 µL) dissolved in 10 mL of methylene chloride during 10 min. Then a solution of mixture of 4'-O-(dihydro-pyran-3-ol)-avermectin B₁ monosaccharide (7550 mg) dissolved in 20 mL of methylene chloride is added over a period of 15 minutes at −75° C. The mixture is stirred at this temperature for 30 min and triethylamine (3560 µL) was added. The mixture is stirred for 10 additional minutes at −75° C. then, the reaction mixture is allowed to come to 0° C. The reaction is quenched with aqueous NaHCO₃ and the aqueous phase is extracted with diethyl ether (×3). The organic phase is dried over Na₂SO₄ and concentrated in vacuo. Flash chromatography (hexane-ethyl acetate 1:3) affords two of epimers of 4'-O-(dihydro-pyran-3-one)-avermectin B₁ monosaccharide which can be isolated and characterized by them mass and NMR spectra.

Step D: To a solution of 4'-O-(dihydro-pyran-3-one)-avermectin B₁ monosaccharide (90 mg) in THF (2.5 ml) is added HF-pyridine solution (500 µl). The mixture is stirred for 18 h at room temperature, poured into saturated aqueous NaHCO₃, extracted with ethyl acetate, dried over Na₂SO₄ and concentrated in vacuo. Flash chromatography (hexane-ethyl acetate 1:2 to 0:1) affords 4'-O-(dihydro-pyran-3-one)-avermectin B₁ monosaccharide which is characterized by its mass and NMR spectra.

4'-O-(dihydro-pyran-3-one)-avermectin B₁ monosaccharide:

First epimer: $B_{1a}$ $C_{46}H_{66}O_{13}$, MW: 826.5. LCMS: $t_{RT}$, 11.69 min., 827.5 (M+H); 849.3 (M+Na).

Second epimer: $B_{1a}$ $C_{46}H_{66}O_{13}$, MW: 826.5. LCMS: $t_{RT}$, 10.94 min., 849.4 (M+Na); 844.5 (M+NH₄).

Example P.13

The compounds listed in tables can also be prepared analogously to the above Preparation Examples or by other methods known to the person skilled in the art.

TABLE 1

Compounds of formula

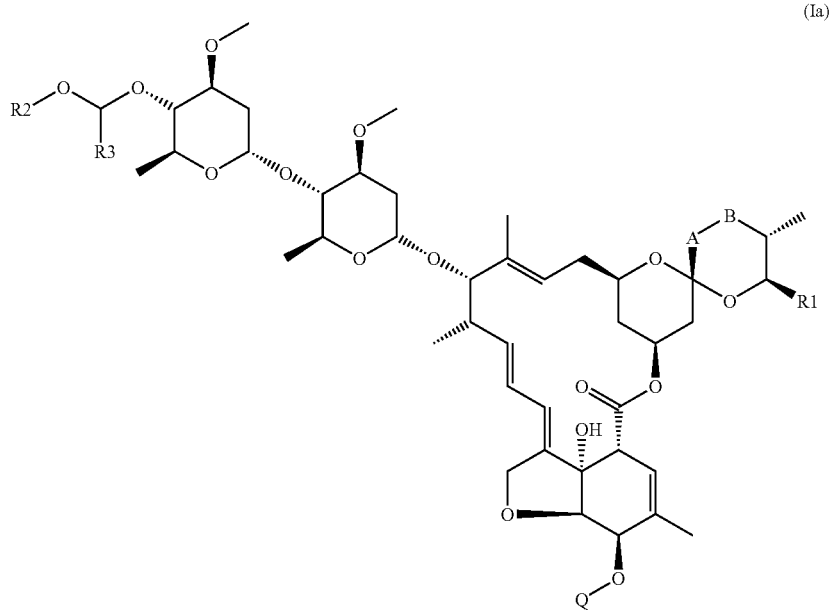

(Ia)

wherein R₁ is sec-butyl (B1a) or isopropyl (B1b), A-B is —CH=CH— and Q is hydrogen:

| No. | R₂ | R₃ | Retention time (min) B1a | B1b |
|---|---|---|---|---|
| 1.1 | CH₂C₆H₅ | H | 12.16 | 11.64 |
| 1.2 | p-ClC₆H₅ | H | | |

TABLE 1-continued

| | | | | |
|---|---|---|---|---|
| 1.3 | (CH$_2$)$_7$CH$_3$ | H | | |
| 1.4 | (CH$_2$)$_3$CH$_3$ | H | | |
| 1.5 | CH$_2$CH$_3$ | H | 10.02 | 9.36 |
| 1.6 | CH$_3$ | H | 10.49 | |
| 1.7 | CH(CH$_3$)$_2$ | H | | |
| 1.8 | CH$_2$CH$_2$OCH$_3$ | H | 10.46 | 9.72 |
| 1.9 | CH$_2$CH$_2$OH | H | 8.53 | |
| 1.10 | CH(CH$_3$)CH$_2$OH | H | | |
| 1.11 | CH$_2$CH$_2$CH$_2$OH | H | 10.98 | 10.67 |
| 1.12 | CH(CH$_3$)CH$_2$CH$_2$OH | H | | |
| 1.13 | CH$_2$CH$_2$OC(=O)CH$_3$ | H | 10.08 | 9.39 |
| 1.14 | CH$_2$(CH$_2$)$_2$OC(=O)CH$_3$ | H | 11.18 | 10.50 |
| 1.15 | CH(CH$_3$)CH$_2$OC(=O)CH$_3$ | H | | |
| 1.16 | CH(CH$_3$)(CH$_2$)$_2$OC(=O)CH$_3$ | H | | |
| 1.17 | CH$_2$CH$_2$N$_3$ | H | | |
| 1.18 | CH$_2$(CH$_2$)$_2$N$_3$ | H | 16.16 | |
| 1.19 | CH$_2$CH$_2$NH$_2$ | H | 6.19 | 5.66 |
| 1.20 | CH$_2$CH$_2$OCH$_2$OCH$_3$ | H | | |
| 1.21 | [CH$_2$CH$_2$CH$_2$-1,2,3-triazole-4,5-bis(CO$_2$Me)] | H | | |
| 1.22 | n-Pr | H | | |
| 1.23 | n-Hexyl | H | | |
| 1.24 | CH(CH$_3$)CH$_2$N$_3$ | H | | |
| 1.25 | CH$_2$CH$_2$OC(=O)OCH$_3$ | H | | |
| 1.26 | CH$_2$CH$_2$OC(=O)NHCH$_3$ | H | | |
| 1.27 | CH$_2$CH$_2$OC(=O)N(CH$_3$)$_2$ | H | | |
| 1.28 | CH$_2$CH$_2$NHC(=O)NHCH$_3$ | H | | |
| 1.29 | CH$_2$CH$_2$NHC(=O)NHC$_6$H$_5$ | H | | |
| 1.30 | CH$_2$CH$_2$NHC(=O)OC$_6$H$_5$ | H | | |
| 1.31 | CH$_2$CH$_2$NHC(=S)NHC$_6$H$_5$ | H | | |
| 1.32 | CH$_2$CH$_2$NHC(=O)OCH$_3$ | H | | |
| 1.33 | CH$_2$CH$_2$NHC(=O)NHCH$_3$ | H | | |
| 1.34 | CH$_2$CH$_2$NHC(=O)N(CH$_3$)$_2$ | H | | |
| 1.35 | CH$_2$CH$_2$NHC(=S)NHCH$_3$ | H | | |
| 1.36 | CH$_2$CH$_2$NHCH$_3$ | H | | |
| 1.37 | CH$_2$CH$_2$N(CH$_3$)$_2$ | H | | |
| 1.38 | CH$_2$CH$_2$SCH$_3$ | H | 10.08 | 9.33 |
| 1.39 | CH$_2$CH$_2$S(O)CH$_3$ | H | 7.09 | 6.45 |
| 1.40 | CH$_2$CH$_2$S(O)$_2$CH$_3$ | H | 7.47 | 6.88 |
| 1.41 | CH$_3$ | CH$_2$Br | | |
| 1.42 | CH$_2$CH=CH$_2$ | CH$_2$Br | | |
| 1.43 | CH$_2$CH$_2$SCH$_2$CH$_3$ | H | 13.28 | 12.59 |
| 1.44 | CH$_2$CH$_2$S(O)CH$_2$CH$_3$ | H | 9.87 | 8.91 |
| 1.45 | CH$_2$CH$_2$S(O)$_2$CH$_2$CH$_3$ | H | 10.72 | 10.03 |
| 1.46 | CH$_2$CH$_2$NHCHO | H | | |
| 1.47 | CH$_2$CH$_2$NH(C=O)CH$_3$ | H | | |
| 1.48 | CH$_2$CH$_2$NH(C=O)OCH$_3$ | H | | |
| 1.49 | CH$_2$CH$_2$NH(C=O)OCH$_2$CH$_3$ | H | | |
| 1.50 | CH$_2$CH$_2$NH(C=O)CH$_2$OCH$_3$ | H | | |
| 1.51 | CH$_2$CH$_2$NH(C=O)CH$_2$CO$_2$CH$_3$ | H | | |
| 1.52 | CH$_2$CH$_2$NH(C=O)OCH$_2$CH=CH$_2$ | H | | |
| 1.53 | CH$_2$CH$_2$OCH$_2$CH=CH$_2$ | H | | |
| 1.54 | CH$_2$CH$_2$SCH$_3$ | H | | |
| 1.55 | CH$_2$CH$_2$S(O)CH$_3$ | H | | |
| 1.56 | CH$_2$CH$_2$S(O)$_2$CH$_3$ | H | | |
| 1.57 | CH$_2$CH$_2$NH(C=O)CH$_2$OCH$_3$ | H | | |
| 1.58 | CH$_2$CH$_2$NH(C=O)CH$_2$CO$_2$CH$_3$ | H | | |
| 1.59 | CH$_2$CH$_2$NH(C=O)OCH$_2$CH=CH$_2$ | H | | |
| 1.60 | CH$_2$CH$_2$OCH$_2$CH=CH$_2$ | H | | |
| 1.61 | CH$_2$CH$_2$SCH$_3$ | H | | |
| 1.62 | CH$_2$CH$_2$S(O)CH$_3$ | H | | |
| 1.63 | CH$_2$CH$_2$S(O)$_2$CH$_3$ | H | | |
| 1.64 | —CH$_2$CH$_2$CH$_2$— | | | |
| 1.65 | —CH$_2$CH$_2$CH$_2$CH$_2$— | | | |
| 1.66 | —CH$_2$CH$_2$—O—CH$_2$— | | | |
| 1.67 | —CH$_2$CH$_2$—N(CH$_3$)—CH$_2$— | | | |
| 1.68 | —CH$_2$(C=O)CH$_2$CH$_2$— | | | |

TABLE 2

Compounds of formula

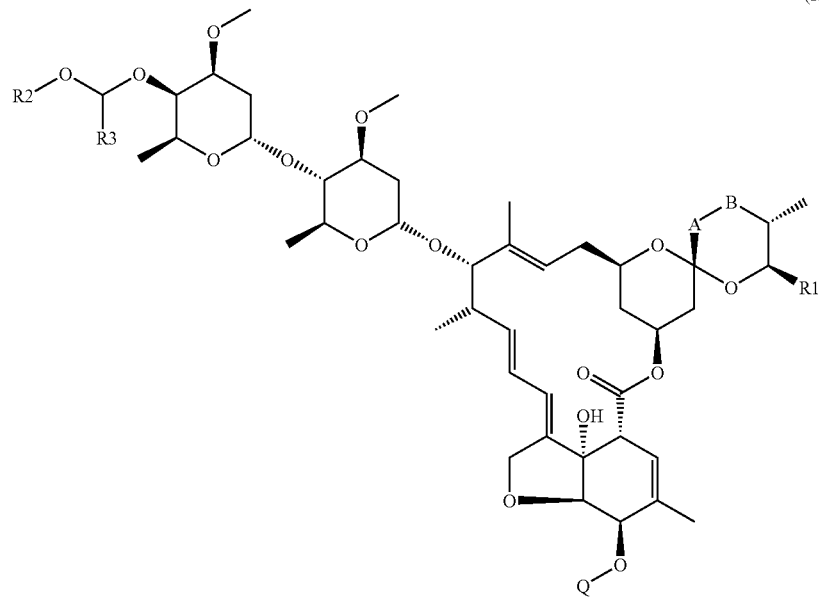

(Ib)

wherein $R_1$ is sec-butyl (B1a) or isopropyl (B1b), A-B is —CH=CH— and Q is hydrogen:

| No. | $R_2$ | $R_3$ | Retention time (min) B1a | B1b |
|---|---|---|---|---|
| 2.1 | $CH_2C_6H_5$ | H | | |
| 2.2 | $pClC_6H_5$ | H | | |
| 2.3 | $(CH_2)_7CH_3$ | H | | |
| 2.4 | $(CH_2)_3CH_3$ | H | | |
| 2.5 | $CH_2CH_3$ | H | 7.14 | |
| 2.6 | $CH_3$ | H | 9.65 | 8.91 |
| 2.7 | $CH(CH_3)_2$ | H | | |
| 2.8 | $CH_2CH_2OCH_3$ | H | 9.39 | 8.69 |
| 2.9 | $CH_2CH_2OH$ | H | 9.84 | |
| 2.10 | $CH(CH_3)CH_2OH$ | H | | |
| 2.11 | $CH_2CH_2CH_2OH$ | H | | |
| 2.12 | $CH(CH_3)CH_2CH_2OH$ | H | | |
| 2.13 | $CH_2CH_2OC(=O)CH_3$ | H | 11.20 | |
| 2.14 | $CH_2(CH_2)_2OC(=O)CH_3$ | H | 12.42 | 11.72 |
| 2.15 | $CH_2CH_2SCH_2CH_3$ | H | 12.43 | 11.84 |
| 2.16 | $CH_2CH_2S(O)CH_2CH_3$ | H | 8.85 | 8.11 |
| 2.17 | $CH_2CH_2S(O)_2CH_2CH_3$ | H | 9.98 | 9.23 |
| 2.18 | $CH_2CH_2N_3$ | H | 11.52 | |
| 2.19 | $CH_2CH_2NH_2$ | H | 6.09 | |
| 2.20 | $CH_2CH_2NHCHO$ | H | | |
| 2.21 | $CH_2CH_2NH(C=O)CH_3$ | H | | |
| 2.22 | $CH_2CH_2NH(C=O)OCH_3$ | H | | |
| 2.23 | $CH_2CH_2NH(C=O)OCH_2CH_3$ | H | | |
| 2.24 | $CH_2CH_2NH(C=O)CH_2OCH_3$ | H | | |
| 2.25 | $CH_2CH_2NH(C=O)CH_2CO_2CH_3$ | H | | |
| 2.26 | $CH_2CH_2NH(C=O)OCH_2CH=CH_2$ | H | | |
| 2.27 | $CH_2CH_2OCH_2CH=CH_2$ | H | | |
| 2.28 | $CH_2CH_2SCH_3$ | H | | |
| 2.29 | $CH_2CH_2S(O)CH_3$ | H | | |
| 2.30 | $CH_2CH_2S(O)_2CH_3$ | H | | |
| 2.31 | $CH_2CH_2CH_2NH_2$ | H | | |
| 2.32 | $CH_2CH_2NHCH_3$ | H | | |
| 2.33 | $CH_2CH_2N(CH_3)_2$ | H | | |
| 2.34 | $CH_2CH_2N(CH_3)CH_2CH_3$ | H | | |

TABLE 2-continued

| | | |
|---|---|---|
| 2.35 | $CH_2CH_2N^+(CH_3)_2 \cdot C_6H_5CO_2^-$ | H |
| 2.36 | —$CH_2CH_2CH_2$— | |
| 2.37 | —$CH_2CH_2CH_2CH_2$— | |
| 2.38 | —$CH_2CH_2$—O—$CH_2$— | |
| 2.39 | —$CH_2CH_2$—N($CH_3$)—$CH_2$— | |
| 2.40 | —$CH_2$(C=O)$CH_2CH_2$— | |

TABLE 3

Compounds of formula (Ic)

wherein $R_1$ is sec-butyl (B1a) or isopropyl (B1b), A-B is —CH=CH— and Q is hydrogen

| No. | $R_2$ | $R_3$ | Retention time (min) B1a | Retention time (min) B1b |
|---|---|---|---|---|
| 3.1 | $CH_2C_6H_5$ | H | | |
| 3.2 | $pClC_6H_5$ | H | | |
| 3.3 | $(CH_2)_7CH_3$ | H | 13.81 | |
| 3.4 | $(CH_2)_3CH_3$ | H | 11.36 | 10.61 |
| 3.5 | $CH_2CH_3$ | H | | |
| 3.6 | $CH_3$ | H | 9.39 | 8.69 |
| 3.7 | $CH(CH_3)_2$ | H | 11.20 | 10.45 |
| 3.8 | $CH_2CH_2OCH_3$ | H | | |
| 3.9 | $CH_2CH_2OH$ | H | 6.99 | 6.35 |
| 3.10 | $CH(CH_3)CH_2OH$ | H | 8.64 | 7.95 |
| 3.11 | $CH_2CH_2CH_2OH$ | H | 7.43 | 6.72 |
| 3.12 | $CH(CH_3)CH_2CH_2OH$ | H | 8.70 | 8.00 |
| 3.13 | $CH_2CH_2OC(=O)CH_3$ | H | 8.48 | 7.79 |
| 3.14 | $CH_2(CH_2)_2OC(=O)CH_3$ | H | 9.28 | 8.64 |
| 3.15 | $CH(CH_3)CH_2OC(=O)CH_3$ | H | 9.44 | 8.75 |
| 3.16 | $CH(CH_3)(CH_2)_2OC(=O)CH_3$ | H | 9.71 | 9.07 |
| 3.17 | $CH_2CH_2N_3$ | H | 9.76 | 9.01 |
| 3.18 | $CH_2(CH_2)_2N_3$ | H | 10.89 | 10.09 |
| 3.19 | $CH_2CH_2NH_2$ | H | 4.11 | |
| 3.20 | $CH_2HC_2OCH_2OCH_3$ | H | 8.69 | 7.89 |
| 3.21 | $MeO_2C$—[triazole ring with $CO_2Me$]—$CH_2CH_2CH_2$—N | H | 9.65 | 8.96 |
| 3.22 | $CH(CH_3)CH_2CH_2OH$ | H | 8.69, 9.28 | 8.00 |
| 3.23 | $CH(CH_3)CH_2CH_2N_3$ | H | 11.04 | 10.35 |
| 3.24 | $CH_2CH_2SCH_3$ | H | 10.08 | 9.33 |
| 3.25 | $CH_2CH_2S(O)CH_3$ | H | 7.09 | 6.45 |
| 3.26 | $CH_2CH_2S(O)_2CH_3$ | H | 7.47 | 6.88 |
| 3.27 | $CH_2CH_2NHCHO$ | H | 7.73 | 6.93 |
| 3.28 | $CH_2CH_2NH(C=O)CH_3$ | H | 7.84 | 7.04 |
| 3.29 | $CH_2CH_2NH(C=O)OCH_3$ | H | 8.69 | |
| 3.30 | $CH_2CH_2NH(C=O)OCH_2CH_3$ | H | 9.29 | |
| 3.31 | $CH_2CH_2NH(C=O)CH_2OCH_3$ | H | 8.16 | 7.41 |
| 3.32 | $CH_2CH_2NH(C=O)CH_2CO_2CH_3$ | H | 7.57 | 6.99 |
| 3.33 | $CH_2CH_2NH(C=O)OCH_2CH=CH_2$ | H | 9.33 | 8.75 |
| 3.34 | $CH_2CH_2OCH_2CH=CH_2$ | H | 11.36 | 10.61 |
| 3.35 | $CH_2CH_2SCH_2CH_3$ | H | 12.11 | 11.41 |
| 3.36 | $CH_2CH_2S(O)CH_2CH_3$ | H | 8.08 | |
| 3.37 | $CH_2CH_2S(O)_2CH_2CH_3$ | H | 8.32 | 7.57 |
| 3.38 | $CH_2CH_2CH_2NH_2$ | H | 4.69 | 4.37 |
| 3.39 | $CH_2CH_2NHCH_3$ | H | | |
| 3.40 | $CH_2CH_2N(CH_3)_2$ | H | 4.69 | 4.48 |
| 3.41 | $CH_2CH_2N(CH_3)CH_2CH_3$ | H | | |
| 3.42 | $CH_2CH_2N^+(CH_3)_2 \cdot C_6H_5CO_2^-$ | H | | |
| 3.43 | $CH_3$ | $CH_2Br$ | 10.56, 10.35 | |
| 3.44 | $CH_2CH=CH_2$ | $CH_2Br$ | 11.26, 11.09 | 10.7, 10.6 |
| 3.45 | —$CH_2CH_2CH_2$— | | 9.07/ 9.49 | 10.45/ 10.93 |
| 3.46 | —$CH_2CH_2$—O—$CH_2$— | | 10.07 | |
| 3.47 | —$CH_2CH_2$—N($CH_3$)—$CH_2$— | | | |
| 3.48 | —$CH_2$(C=O)$CH_2CH_2$— | | 10.94/ 11.69 | |
| 3.49 | —$CH_2CH(CH_3)CH_2$— | | 9.98/ 10.51 | |
| 3.50 | —$CH_2CH_2CH(CH_3)CH_2$— | | 11.87 | 11.20 |

TABLE 4

Compounds of formula

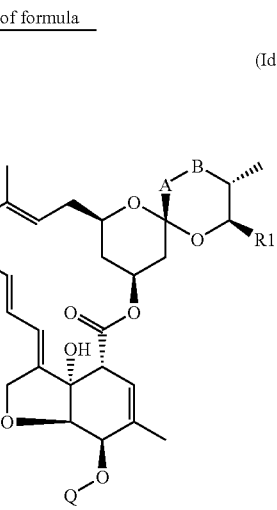

(Id)

wherein $R_1$ is sec-butyl (B1a) or isopropyl (B1b), A-B is —CH=CH— and Q is hydrogen:

| No. | $R_2$ | $R_3$ | Retention time (min) B1a | B1b |
|---|---|---|---|---|
| 4.1 | $CH_2C_6H_5$ | H | 10.72 | 10.03 |
| 4.2 | $pClC_6H_5$ | H | 11.63 | |
| 4.3 | $(CH_2)_7CH_3$ | H | 13.71 | 13.17 |
| 4.4 | $(CH_2)_3CH_3$ | H | 11.15 | 10.29 |
| 4.5 | $CH_2CH_3$ | H | | |
| 4.6 | $CH_3$ | H | | |
| 4.7 | $CH(CH_3)_2$ | H | 9.92 | 9.17 |
| 4.8 | $CH_2CH_2OCH_3$ | H | | |
| 4.9 | $CH_2CH_2OH$ | H | 6.24 | 5.66 |
| 4.10 | $CH(CH_3)CH_2OH$ | H | 6.94 | 6.45 |
| 4.11 | $CH_2CH_2CH_2OH$ | H | 6.45 | 5.87 |
| 4.12 | $CH(CH_3)CH_2CH_2OH$ | H | 6.89 | 6.25 |
| 4.13 | $CH_2CH_2OC(=O)CH_3$ | H | 8.16 | 7.57 |
| 4.14 | $CH_2(CH_2)_2OC(=O)CH_3$ | H | 8.69 | 8.05 |
| 4.15 | $CH(CH_3)CH_2OC(=O)CH_3$ | H | 8.49 | 7.95 |
| 4.16 | $CH(CH_3)(CH_2)_2OC(=O)CH_3$ | H | 8.97 | 8.32 |
| 4.17 | $CH_2CH_2N_3$ | H | 8.75 | 8.11 |
| 4.18 | $CH_2(CH_2)_2N_3$ | H | 9.33 | 8.69 |
| 4.19 | $CH_2CH_2NH_2$ | H | 11.09 | 10.35 |
| 4.20 | $CH_2CH_2SCH_2CH_3$ | H | 11.20 | 10.51 |
| 4.21 | $CH_2CH_2S(O)CH_2CH_3$ | H | 6.93 | 6.29 |
| 4.22 | $CH_2CH_2S(O)_2CH_2CH_3$ | H | 8.11 | 7.52 |
| 4.23 | $CH(CH_3)CH_2CH_2N_3$ | H | | |
| 4.24 | $CH_2CH_2SCH_3$ | H | | |
| 4.25 | $CH_2CH_2S(O)CH_3$ | H | | |
| 4.26 | $CH_2CH_2S(O)_2CH_3$ | H | | |
| 4.27 | $CH_2CH_2NHCHO$ | H | | |
| 4.28 | $CH_2CH_2NH(C=O)CH_3$ | H | | |
| 4.29 | $CH_2CH_2NH(C=O)OCH_3$ | H | | |
| 4.30 | $CH_2CH_2NH(C=O)OCH_2CH_3$ | H | | |
| 4.31 | $CH_2CH_2NH(C=O)CH_2OCH_3$ | H | | |
| 4.32 | $CH_2CH_2NH(C=O)CH_2CO_2CH_3$ | H | | |
| 4.33 | $CH_2CH_2NH(C=O)OCH_2CH=CH_2$ | H | | |
| 4.34 | $CH_2CH_2OCH_2CH=CH_2$ | H | | |
| 4.35 | $CH_2CH_2CH_2NH_2$ | H | | |
| 4.36 | $CH_2CH_2NHCH_3$ | H | | |
| 4.37 | $CH_2CH_2N(CH_3)_2$ | H | | |
| 4.38 | $CH_2CH_2N(CH_3)CH_2CH_3$ | H | | |
| 4.39 | $CH_2CH_2N^+(CH_3)_2 \cdot C_6H_5CO_2^-$ | H | | |
| 4.40 | —$CH_2CH_2CH_2$— | | | |
| 4.41 | —$CH_2CH_2CH_2CH_2$— | | 10.26/11.03 | |
| 4.42 | —$CH_2CH_2$—O—$CH_2$— | | | |
| 4.43 | —$CH_2CH_2$—N($CH_3$)—$CH_2$— | | | |
| 4.44 | —$CH_2(C=O)CH_2CH_2$— | | | |

TABLE A

Compounds of the formula (I)

| No. | $R_2$ | $R_3$ |
|---|---|---|
| A.1 | $CH_2C_6H_5$ | H |
| A.2 | $p-ClC_6H_5$ | H |
| A.3 | $(CH_2)_7CH_3$ | H |
| A.4 | $(CH_2)_3CH_3$ | H |
| A.5 | $CH_2CH_3$ | H |
| A.6 | $CH_3$ | H |
| A.7 | $CH(CH_3)_2$ | H |
| A.8 | $CH_2CH_2OCH_3$ | H |
| A.9 | $CH_2CH_2OH$ | H |
| A.10 | $CH(CH_3)CH_2OH$ | H |
| A.11 | $CH_2CH_2CH_2OH$ | H |
| A.12 | $CH(CH_3)CH_2CH_2OH$ | H |
| A.13 | $CH_2CH_2OC(=O)CH_3$ | H |
| A.14 | $CH_2(CH_2)_2OC(=O)CH_3$ | H |
| A.15 | $CH(CH_3)CH_2OC(=O)CH_3$ | H |
| A.16 | $CH(CH_3)(CH_2)_2OC(=O)CH_3$ | H |
| A.17 | $CH_2CH_2N_3$ | H |
| A.18 | $CH_2(CH_2)_2N_3$ | H |
| A.19 | $CH_2CH_2NH_2$ | H |
| A.20 | $CH_2CH_2OCH_2OCH_3$ | H |
| A.21 | $CH_2CH_2CH_2$— triazole with $MeO_2C$ and $CO_2Me$ substituents | H |
| A.22 | n-Pr | H |
| A.23 | n-Hexyl | H |
| A.24 | $CH(CH_3)CH_2CH_2N_3$ | H |

TABLE A-continued

Compounds of the formula (I)

| No. | $R_2$ | $R_3$ |
|---|---|---|
| A.25 | $CH_2CH_2OC(=O)OCH_3$ | H |
| A.26 | $CH_2CH_2OC(=O)NHCH_3$ | H |
| A.27 | $CH_2CH_2OC(=O)N(CH_3)_2$ | H |
| A.28 | $CH_2CH_2NHC(=O)NHCH_3$ | H |
| A.29 | $CH_2CH_2NHC(=O)NHC_6H_5$ | H |
| A.30 | $CH_2CH_2NHC(=O)OC_6H_5$ | H |
| A.31 | $CH_2CH_2NHC(=S)NHC_6H_5$ | H |
| A.32 | $CH_2CH_2NHC(=O)OCH_3$ | H |
| A.33 | $CH_2CH_2NHC(=O)NHCH_3$ | H |
| A.34 | $CH_2CH_2NHC(=O)N(CH_3)_2$ | H |
| A.35 | $CH_2CH_2NHC(=S)NHCH_3$ | H |
| A.36 | $CH_2CH_2NHCH_3$ | H |
| A.37 | $CH_2CH_2N(CH_3)_2$ | H |
| A.38 | $CH_2CH_2SCH_3$ | H |
| A.39 | $CH_2CH_2S(O)CH_3$ | H |
| A.40 | $CH_2CH_2S(O)_2CH_3$ | H |
| A.41 | $CH_3$ | $CH_2Br$ |
| A.42 | $CH_2CH=CH_2$ | $CH_2Br$ |
| A.43 | $CH_2CH_2NHCHO$ | H |
| A.44 | $CH_2CH_2N(CH_3)CHO$ | H |
| A.45 | $CH_2CH_2NHCH_2COOCH_3$ | H |
| A.46 | $CH_2COCH_3$ | H |
| A.47 | $-CH_2-CH_2-NH-C(=O)-CH_3$ | H |
| A.48 | $-CH_2-CH_2-NH-C(=O)-CH_2-O-CH_3$ | H |
| A.49 | $-CH_2-CH_2-N(CH_3)-C(=O)-CH_3$ | H |
| A.50 | $-CH_2-CH_2-N(CH_3)-C(=O)-CH_2-O-CH_3$ | H |
| A.51 | $-CH_2-CH_2-CH_2-NH-C(=O)-H$ | H |
| A.52 | $-CH_2-CH_2-CH_2-NH-C(=O)-CH_3$ | H |
| A.53 | $-CH_2-CH_2-CH_2-NH-C(=O)-CH_2-O-CH_3$ | H |
| A.54 | $-CH_2-CH_2-CH_2-N(CH_3)-C(=O)-H$ | H |
| A.55 | $-CH_2-CH_2-CH_2-N(CH_3)-C(=O)-CH_3$ | H |
| A.56 | $-CH_2-CH_2-CH_2-N(CH_3)-C(=O)-CH_2-O-CH_3$ | H |
| A.57 | $-CH_2-CH_2-N(CH_3)-CH_2-CH_3$ | H |
| A.58 | $-CH_2-CH_2-N(CH_3)-CH_2-CH=CH_2$ | H |
| A.59 | $-CH_2-CH_2-N(CH_3)-CH_2-C(=O)-O-CH_2-CH_3$ | H |
| A.60 | $-CH_2-CH_2-N(CH_3)-CH_2-C_6H_5$ | H |
| A.61 | 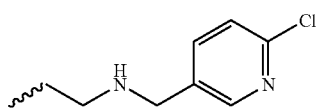 | H |
| A.62 | $-CH_2-CH_2-N(CH_3)-CN$ | H |
| A.63 | $-CH_2-CH_2-N(CH_3)-CH_2-CH_2-OH$ | H |
| A.64 | 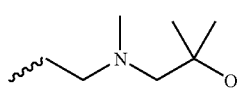 | H |
| A.65 | 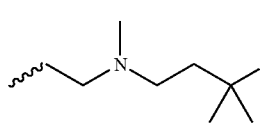 | H |
| A.66 | 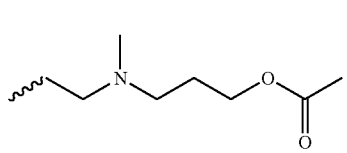 | H |

TABLE A-continued

Compounds of the formula (I)

| No. | R₂ | R₃ |
|---|---|---|
| A.67 | —CH₂—CH₂—N(CH₃)—CH₂—C≡CH | H |
| A.68 | —CH₂—CH₂—NH—SO₂—CH₃ | H |
| A.69 | —CH₂—CH₂—NH—CH₂—CH₂—CN | H |
| A.70 | —CH₂—CH₂—N(CH₃)—CH(CH₃)₂ | H |
| A.71 | 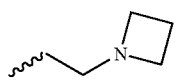 | H |
| A.72 | 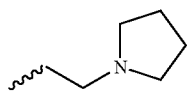 | H |
| A.73 | 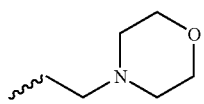 | H |
| A.74 | 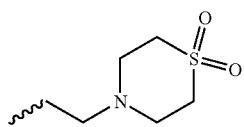 | H |
| A.75 | 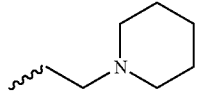 | H |
| A.76 | 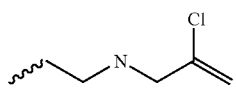 | H |
| A.77 | 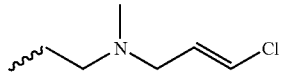 | H |
| A.78 | CH₂CH₂CH₂ | |
| A.79 | CH₂CH₂CH₂CH₂ | |

Table 5: Compounds of the formula (Ia) wherein $R_1$ is sec-butyl or isopropyl, A-B is —CH=CH—, Q is TBDMS and the combination of the substituents $R_2$ and $R_3$ for each compound corresponds to a line A.1 to A.79 of table A.

Table 6: Compounds of the formula (Ia) wherein $R_1$ is sec-butyl or isopropyl, A-B is —CH₂—CH₂—, Q is TBDMS and the combination of the substituents $R_2$ and $R_3$ for each compound corresponds to a line A.1 to A.79 of table A.

Table 7: Compounds of the formula (Ia) wherein $R_1$ is sec-butyl or isopropyl, A-B is —CH=CH—, Q is H and the combination of the substituents $R_2$ and $R_3$ for each compound corresponds to a line A.1 to A.79 of table A.

Table 8: Compounds of the formula (Ia) wherein $R_1$ is sec-butyl or isopropyl, A-B is —CH₂—CH₂—, Q is H and the combination of the substituents $R_2$ and $R_3$ for each compound corresponds to a line A.1 to A.79 of table A.

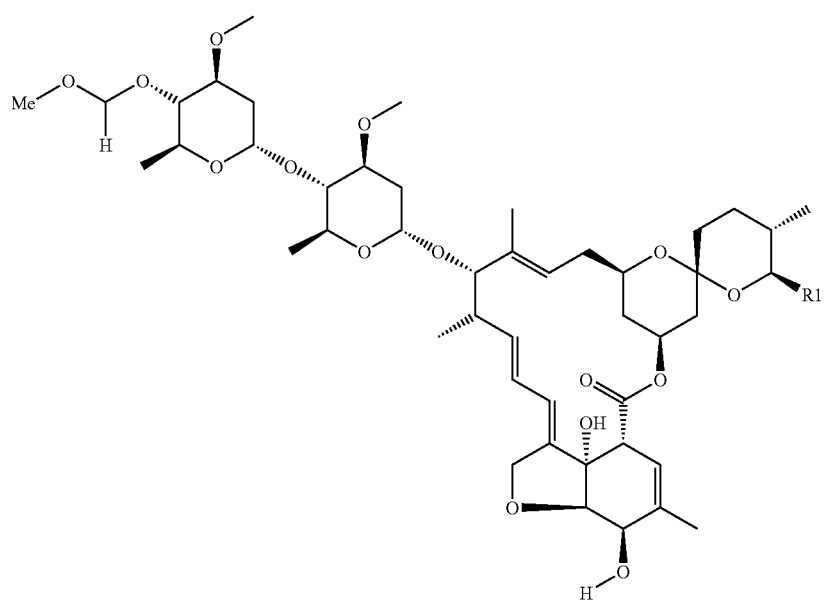

Retention time in HPLC analysis for derivative wherein $R_1$ is sec-butyl: 13.83 min. Retention time in HPLC analysis for derivative wherein $R_1$ is isopropyl: 13.40 min.

Table 9: Compounds of the formula (Ia) wherein $R_1$ is cyclohexyl, A-B is —CH=CH—, Q is TBDMS and the combination of the substituents $R_2$ and $R_3$ for each compound corresponds to a line A.1 to A.79 of table A.

Table 10: Compounds of the formula (Ia) wherein $R_1$ is cyclohexyl, A-B is —CH$_2$—CH$_2$—, Q is TBDMS and the combination of the substituents $R_2$ and $R_3$ for each compound corresponds to a line A.1 to A.79 of table A.

Table 11: Compounds of the formula (Ia) wherein $R_1$ is cyclohexyl, A-B is —CH=CH—, Q is H and the combination of the substituents $R_2$ and $R_3$ for each compound corresponds to a line A.1 to A.79 of table A.

Retention time in HPLC analysis 12.43 min.

Table 12: Compounds of the formula (Ia) wherein $R_1$ is cyclohexyl, A-B is —CH$_2$—CH$_2$—, Q is H and the combination of the substituents $R_2$ and $R_3$ for each compound corresponds to a line A.1 to A.79 of table A.

Table 13: Compounds of the formula (Ia) wherein $R_1$ is 1-methyl-butyl, A-B is —CH=CH—, Q is TBDMS and the combination of the substituents $R_2$ and $R_3$ for each compound corresponds to a line A.1 to A.79 of table A.

Table 14: Compounds of the formula (Ia) wherein $R_1$ is 1-methyl-butyl, A-B is —CH$_2$—CH$_2$—, Q is TBDMS and the combination of the substituents $R_2$ and $R_3$ for each compound corresponds to a line A.1 to A.79 of table A.

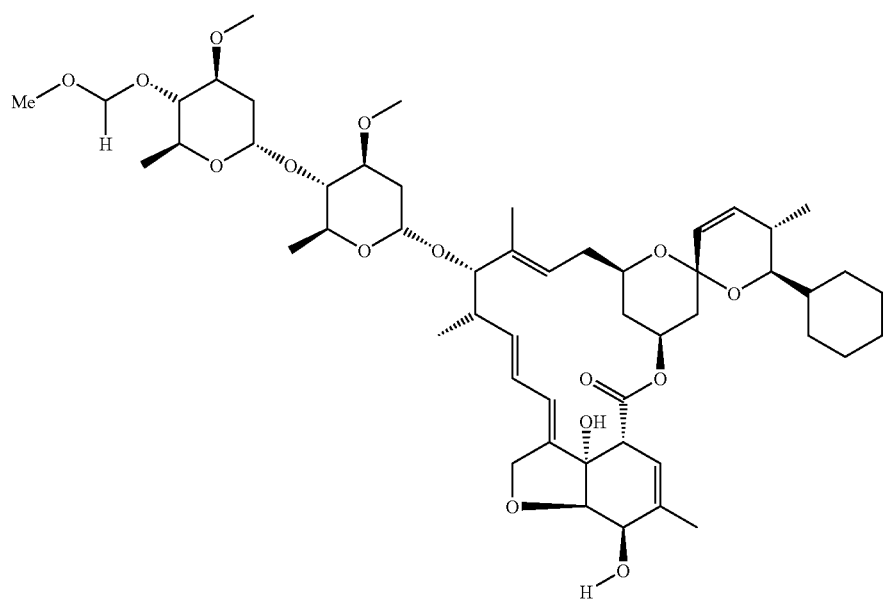

Table 15: Compounds of the formula (Ia) wherein $R_1$ is 1-methyl-butyl, A-B is —CH=CH—, Q is H and the combination of the substituents $R_2$ and $R_3$ for each compound corresponds to a line A.1 to A.79 of table A.

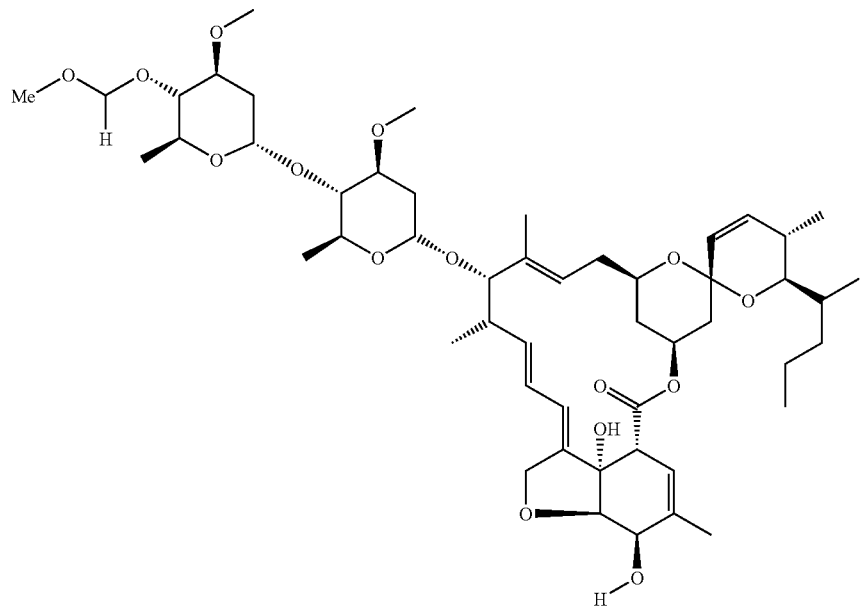

Retention time in HPLC analysis: 13.37 min.

Table 16: Compounds of the formula (Ia) wherein $R_1$ is 1-methyl-butyl, A-B is —CH$_2$—CH$_2$—, Q is H and the combination of the substituents $R_2$ and $R_3$ for each compound corresponds to a line A.1 to A.79 of table A.

Table 17: Compounds of the formula (Ia) wherein $R_1$ is ethyl, A-B is —CH=CH—, Q is TBDMS and the combination of the substituents $R_2$ and $R_3$ for each compound corresponds to a line A.1 to A.79 of table A.

Table 18: Compounds of the formula (Ia) wherein $R_1$ is ethyl, A-B is —CH$_2$—CH$_2$—, Q is TBDMS and the combination of the substituents $R_2$ and $R_3$ for each compound corresponds to a line A.1 to A.79 of table A.

Table 19: Compounds of the formula (Ia) wherein $R_1$ is ethyl, A-B is —CH=CH—, Q is H and the combination of the substituents $R_2$ and $R_3$ for each compound corresponds to a line A.1 to A.79 of table A.

Table 20: Compounds of the formula (Ia) wherein $R_1$ is ethyl, A-B is —CH$_2$—CH$_2$—, Q is H and the combination of the substituents $R_2$ and $R_3$ for each compound corresponds to a line A.1 to A.79 of table A.

Table 21: Compounds of the formula (Ia) wherein $R_1$ is methyl, A-B is —CH=CH—, Q is TBDMS and the combination of the substituents $R_2$ and $R_3$ for each compound corresponds to a line A.1 to A.79 of table A.

Table 22: Compounds of the formula (Ia) wherein $R_1$ is methyl, A-B is —CH$_2$—CH$_2$—, Q is TBDMS and the combination of the substituents $R_2$ and $R_3$ for each compound corresponds to a line A.1 to A.79 of table A.

Table 23: Compounds of the formula (Ia) wherein $R_1$ is methyl, A-B is —CH=CH—, Q is H and the combination of the substituents $R_2$ and $R_3$ for each compound corresponds to a line A.1 to A.79 of table A.

Table 24: Compounds of the formula (Ia) wherein $R_1$ is methyl, A-B is —CH$_2$—CH$_2$—, Q is H and the combination of the substituents $R_2$ and $R_3$ for each compound corresponds to a line A.1 to A.79 of table A.

Table 25: Compounds of the formula (Ia) wherein $R_1$ is i-propyl, A-B is —CH=CH—, Q is TBDMS and the combination of the substituents $R_2$ and $R_3$ for each compound corresponds to a line A.1 to A.79 of table A.

Table 26: Compounds of the formula (Ia) wherein $R_1$ is i-propyl, A-B is —CH$_2$—CH$_2$—, Q is TBDMS and the combination of the substituents $R_2$ and $R_3$ for each compound corresponds to a line A.1 to A.79 of table A.

Table 27: Compounds of the formula (Ia) wherein $R_1$ is i-propyl, A-B is —CH=CH—, Q is H and the combination of the substituents $R_2$ and $R_3$ for each compound corresponds to a line A.1 to A.79 of table A.

Table 28: Compounds of the formula (Ia) wherein $R_1$ is i-propyl, A-B is —CH$_2$—CH$_2$—, Q is H and the combination of the substituents $R_2$ and $R_3$ for each compound corresponds to a line A.1 to A.79 of table A.

Table 29: Compounds of the formula (Ib) wherein $R_1$ is sec-butyl or isopropyl, A-B is —CH—CH—, Q is TBDMS and the combination of the substituents $R_2$ and $R_3$ for each compound corresponds to a line A.1 to A.79 of table A.

Table 30: Compounds of the formula (Ib) wherein $R_1$ is sec-butyl or isopropyl, A-B is —CH$_2$—CH$_2$—, Q is TBDMS and the combination of the substituents $R_2$ and $R_3$ for each compound corresponds to a line A.1 to A.79 of table A.

Table 31: Compounds of the formula (Ib) wherein $R_1$ is sec-butyl or isopropyl, A-B is —CH=CH—, Q is H and the combination of the substituents $R_2$ and $R_3$ for each compound corresponds to a line A.1 to A.79 of table A.

Table 32: Compounds of the formula (Ib) wherein $R_1$ is sec-butyl or isopropyl, A-B is —CH$_2$—CH$_2$—, Q is H and the combination of the substituents $R_2$ and $R_3$ for each compound corresponds to a line A.1 to A.79 of table A.

Table 33: Compounds of the formula (Ib) wherein $R_1$ is cyclohexyl, A-B is —CH=CH—, Q is H and the combination of the substituents $R_2$ and $R_3$ for each compound corresponds to a line A.1 to A.79 of table A.

Table 34: Compounds of the formula (Ib) wherein $R_1$ is cyclohexyl, A-B is —CH$_2$—CH$_2$—, Q is TBDMS and the combination of the substituents $R_2$ and $R_3$ for each compound corresponds to a line A.1 to A.79 of table A.

Table 35: Compounds of the formula (Ib) wherein $R_1$ is cyclohexyl, A-B is —CH=CH—, Q is H and the combination of the substituents $R_2$ and $R_3$ for each compound corresponds to a line A.1 to A.79 of table A.

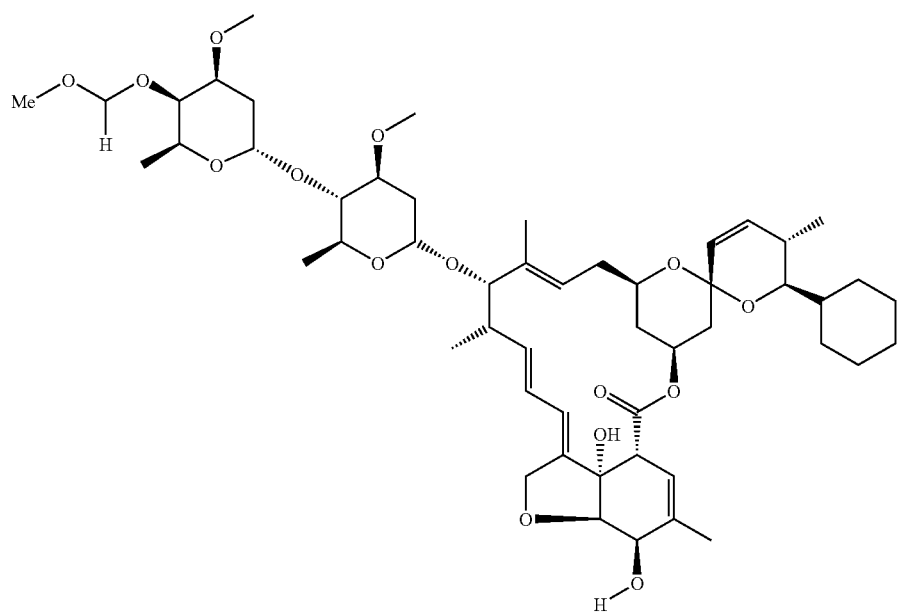

Retention time in HPLC analysis: 11.36 min.

Table 36: Compounds of the formula (Ib) wherein $R_1$ is cyclohexyl, A-B is —$CH_2$—$CH_2$—, Q is H and the combination of the substituents $R_2$ and $R_3$ for each compound corresponds to a line A.1 to A.79 of table A.

Table 37: Compounds of the formula (Ib) wherein $R_1$ is 1-methyl-butyl, A-B is —CH=CH—, Q is TBDMS and the combination of the substituents $R_2$ and $R_3$ for each compound corresponds to a line A.1 to A.79 of table A.

Table 38: Compounds of the formula (Ib) wherein $R_1$ is 1-methyl-butyl, A-B is —$CH_2$—$CH_2$—, Q is TBDMS and the combination of the substituents $R_2$ and $R_3$ for each compound corresponds to a line A.1 to A.79 of table A.

Table 39: Compounds of the formula (Ib) wherein $R_1$ is 1-methyl-butyl, A-B is —CH=CH—, Q is H and the combination of the substituents $R_2$ and $R_3$ for each compound corresponds to a line A.1 to A.79 of table A.

Retention time in HPLC analysis: 12.59 min.

Table 40: Compounds of the formula (Ib) wherein $R_1$ is 1-methyl-butyl, A-B is —$CH_2$—$CH_2$—, Q is H and the combination of the substituents $R_2$ and $R_3$ for each compound corresponds to a line A.1 to A.79 of table A.

Table 41: Compounds of the formula (Ib) wherein $R_1$ is ethyl, A-B is Q is TBDMS and the combination of the substituents $R_2$ and $R_3$ for each compound corresponds to a line A.1 to A.79 of table A.

Table 42: Compounds of the formula (Ib) wherein $R_1$ is ethyl, A-B is —$CH_2$—$CH_2$—, Q is TBDMS and the combination of the substituents $R_2$ and $R_3$ for each compound corresponds to a line A.1 to A.79 of table A.

Table 43: Compounds of the formula (Ib) wherein $R_1$ is ethyl, A-B is —CH=CH—, Q is H and the combination of the substituents $R_2$ and $R_3$ for each compound corresponds to a line A.1 to A.79 of table A.

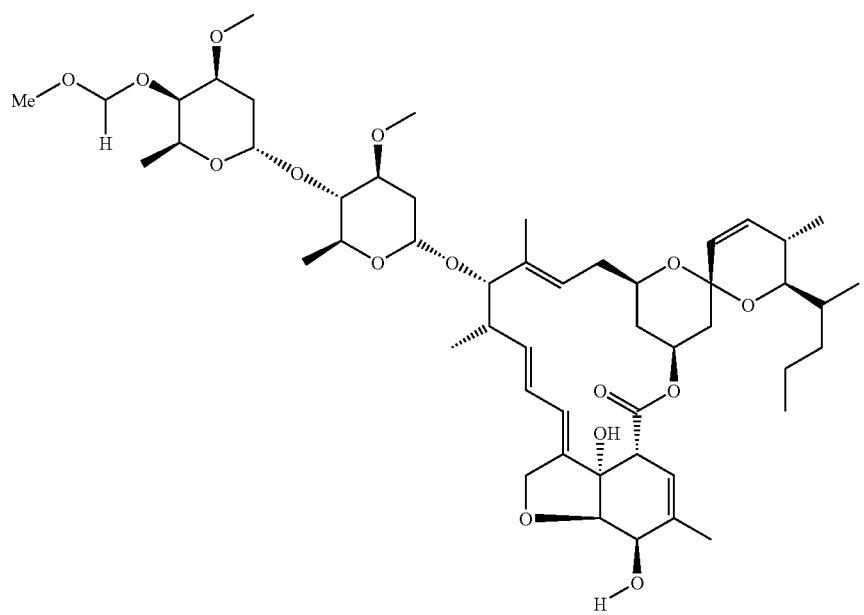

Table 44: Compounds of the formula (Ib) wherein $R_1$ is ethyl, A-B is —$CH_2$—$CH_2$—, Q is H and the combination of the substituents $R_2$ and $R_3$ for each compound corresponds to a line A.1 to A.79 of table A.

Table 45: Compounds of the formula (Ib) wherein $R_1$ is ethyl, A-B is —CH=CH—, Q is TBDMS and the combination of the substituents $R_2$ and $R_3$ for each compound corresponds to a line A.1 to A.79 of table A.

Table 46: Compounds of the formula (Ib) wherein $R_1$ is ethyl, A-B is —$CH_2$—$CH_2$—, Q is TBDMS and the combination of the substituents $R_2$ and $R_3$ for each compound corresponds to a line A.1 to A.79 of table A.

Table 47: Compounds of the formula (Ib) wherein $R_1$ is methyl, A-B is —CH=CH—, Q is TBDMS and the combination of the substituents $R_2$ and $R_3$ for each compound corresponds to a line A.1 to A.79 of table A.

Table 48: Compounds of the formula (Ib) wherein $R_1$ is methyl, A-B is —$CH_2$—$CH_2$—, Q is H and the combination of the substituents $R_2$ and $R_3$ for each compound corresponds to a line A.1 to A.79 of table A.

Table 49: Compounds of the formula (Ib) wherein $R_1$ is -propyl, A-B is —CH=CH—, Q is H and the combination of the substituents $R_2$ and $R_3$ for each compound corresponds to a line A.1 to A.79 of table A.

Table 50: Compounds of the formula (Ib) wherein $R_1$ is -propyl, A-B is —$CH_2$—$CH_2$—, Q is TBDMS and the combination of the substituents $R_2$ and $R_3$ for each compound corresponds to a line A.1 to A.79 of table A.

Table 51: Compounds of the formula (Ib) wherein $R_1$ is i-propyl, A-B is —CH=CH—, Q is TBDMS and the combination of the substituents $R_2$ and $R_3$ for each compound corresponds to a line A.1 to A.79 of table A.

Table 52: Compounds of the formula (Ib) wherein $R_1$ is i-propyl, A-B is —$CH_2$—$CH_2$—, Q is H and the combination of the substituents $R_2$ and $R_3$ for each compound corresponds to a line A.1 to A.79 of table A.

Table 53: Compounds of the formula (Ic) wherein $R_1$ is sec-butyl or isopropyl, A-B is —CH=CH—, Q is TBDMS and the combination of the substituents $R_2$ and $R_3$ for each compound corresponds to a line A.1 to A.79 of table A.

Table 54: Compounds of the formula (Ic) wherein $R_1$ is sec-butyl or isopropyl, A-B is —$CH_2$—$CH_2$—, Q is TBDMS and the combination of the substituents $R_2$ and $R_3$ for each compound corresponds to a line A.1 to A.79 of table A.

Table 55: Compounds of the formula (Ic) wherein $R_1$ is sec-butyl or isopropyl, A-B is —CH=CH—, Q is H and the combination of the substituents $R_2$ and $R_3$ for each compound corresponds to a line A.1 to A.79 of table A.

Table 56: Compounds of the formula (Ic) wherein $R_1$ is sec-butyl or isopropyl, A-B is —$CH_2$—$CH_2$—, Q is H and the combination of the substituents $R_2$ and $R_3$ for each compound corresponds to a line A.1 to A.79 of table A.

| No. | $R_2$ | $R_3$ | Retention time (min) | |
|---|---|---|---|---|
| | | | B1a | B1b |
| 56.6 | $CH_3$ | H | 12.75 | 11.95 |
| 56.7 | $CH(CH_3)_2$ | H | 13.87 | 13.07 |
| 56.78 | $CH_2CH_2CH_2$ | | 12.86, 12.21 | 12.11, 11.57 |

Table 57: Compounds of the formula (Ic) wherein $R_1$ is cyclohexyl, A-B is —CH=CH—, Q is TBDMS and the combination of the substituents $R_2$ and $R_3$ for each compound corresponds to a line A.1 to A.79 of table A.

| No. | $R_2$ | $R_3$ | Retention time (min) |
|---|---|---|---|
| 57.6 | $CH_3$ | H | 15.42 |
| 57.7 | $CH(CH_3)_2$ | H | 15.79 |

Table 58: Compounds of the formula (Ic) wherein $R_1$ is cyclohexyl, A-B is —$CH_2$—$CH_2$—, Q is TBDMS and the combination of the substituents $R_2$ and $R_3$ for each compound corresponds to a line A.1 to A.79 of table A.

Table 59: Compounds of the formula (Ic) wherein $R_1$ is sec-butyl or isopropyl, A-B is —CH=CH—, Q is H and the combination of the substituents $R_2$ and $R_3$ for each compound corresponds to a line A.1 to A.79 of table A.

| No. | $R_2$ | $R_3$ | Retention time (min) |
|---|---|---|---|
| 59.6 | $CH_3$ | H | 11.31 |
| 59.7 | $CH(CH_3)_2$ | H | 12.56 |

Table 60: Compounds of the formula (Ic) wherein $R_1$ is cyclohexyl, A-B is —$CH_2$—$CH_2$—, Q is H and the combination of the substituents $R_2$ and $R_3$ for each compound corresponds to a line A.1 to A.79 of table A.

Table 61: Compounds of the formula (Ic) wherein $R_1$ is 1-methyl-butyl, A-B is —CH=CH—, Q is TBDMS and the combination of the substituents $R_2$ and $R_3$ for each

| No. | $R_2$ | $R_3$ | Retention time (min) |
|---|---|---|---|
| 61.6 | $CH_3$ | H | 15.36 |
| 61.7 | $CH(CH_3)_2$ | H | 15.79 |

Table 62: Compounds of the formula (Ic) wherein $R_1$ is 1-methyl-butyl, A-B is —$CH_2$—$CH_2$—, Q is TBDMS and the combination of the substituents $R_2$ and $R_3$ for each compound corresponds to a line A.1 to A.79 of table A.

Table 63: Compounds of the formula (Ic) wherein $R_1$ is 1-methyl-butyl, A-B is —CH=CH—, Q is H and the combination of the substituents $R_2$ and $R_3$ for each compound corresponds to a line A.1 to A.79 of table A.

| No. | $R_2$ | $R_3$ | Retention time (min) |
|---|---|---|---|
| 63.6 | $CH_3$ | H | 11.09 |
| 63.7 | $CH(CH_3)_2$ | H | 12.27 |

Table 64: Compounds of the formula (Ic) wherein $R_1$ is 1-methyl-butyl, A-B is —$CH_2$—$CH_2$—, Q is H and the combination of the substituents $R_2$ and $R_3$ for each compound corresponds to a line A.1 to A.79 of table A.

Table 65: Compounds of the formula (Ic) wherein $R_1$ is ethyl, A-B is —CH=CH—, Q is TBDMS and the combination of the substituents $R_2$ and $R_3$ for each compound corresponds to a line A.1 to A.79 of table A.

Table 66: Compounds of the formula (Ic) wherein $R_1$ is ethyl, A-B is —$CH_2$—$CH_2$—, Q is TBDMS and the combination of the substituents $R_2$ and $R_3$ for each compound corresponds to a line A.1 to A.79 of table A.

Table 67: Compounds of the formula (Ic) wherein $R_1$ is ethyl, A-B is —CH=CH—, Q is H and the combination of the substituents $R_2$ and $R_3$ for each compound corresponds to a line A.1 to A.79 of table A.

Table 68: Compounds of the formula (Ic) wherein $R_1$ is ethyl, A-B is —$CH_2$—$CH_2$—, Q is H and the combination of the substituents $R_2$ and $R_3$ for each compound corresponds to a line A.1 to A.79 of table A.

Table 69: Compounds of the formula (Ic) wherein $R_1$ is methyl, A-B is —CH=CH—, Q is TBDMS and the combination of the substituents $R_2$ and $R_3$ for each compound corresponds to a line A.1 to A.79 of table A.

Table 70: Compounds of the formula (Ic) wherein $R_1$ is methyl, A-B is —$CH_2$—$CH_2$—, Q is TBDMS and the combination of the substituents $R_2$ and $R_3$ for each compound corresponds to a line A.1 to A.79 of table A.

Table 71: Compounds of the formula (Ic) wherein $R_1$ is methyl, A-B is —CH=CH—, Q is H and the combination of the substituents $R_2$ and $R_3$ for each compound corresponds to a line A.1 to A.79 of table A.

Table 72: Compounds of the formula (Ic) wherein $R_1$ is methyl, A-B is —$CH_2$—$CH_2$—, Q is H and the combination of the substituents $R_2$ and $R_3$ for each compound corresponds to a line A.1 to A.79 of table A.

Table 73: Compounds of the formula (Ic) wherein $R_1$ is i-propyl, A-B is —CH=CH—, Q is TBDMS and the combination of the substituents $R_2$ and $R_3$ for each compound corresponds to a line A.1 to A.79 of table A.

Table 74: Compounds of the formula (Ic) wherein $R_1$ is i-propyl, A-B is —$CH_2$—$CH_2$—, Q is TBDMS and the combination of the substituents $R_2$ and $R_3$ for each compound corresponds to a line A.1 to A.79 of table A.

Table 75: Compounds of the formula (Ic) wherein $R_1$ is i-propyl, A-B is —CH=CH—, Q is H and the combination of the substituents $R_2$ and $R_3$ for each compound corresponds to a line A.1 to A.79 of table A.

Table 76: Compounds of the formula (Ic) wherein $R_1$ is i-propyl, A-B is —$CH_2$—$CH_2$—, Q is H and the combination of the substituents $R_2$ and $R_3$ for each compound corresponds to a line A.1 to A.79 of table A.

Table 77: Compounds of the formula (Id) wherein $R_1$ is sec-butyl or isopropyl, A-B is —CH=CH—, Q is TBDMS and the combination of the substituents $R_2$ and $R_3$ for each compound corresponds to a line A.1 to A.79 of table A.

Table 78: Compounds of the formula (Id) wherein $R_1$ is sec-butyl or isopropyl, A-B is —$CH_2$—$CH_2$—, Q is TBDMS and the combination of the substituents $R_2$ and $R_3$ for each compound corresponds to a line A.1 to A.79 of table A.

Table 79: Compounds of the formula (Id) wherein $R_1$ is sec-butyl or isopropyl, A-B is —CH=CH—, Q is H and the combination of the substituents $R_2$ and $R_3$ for each compound corresponds to a line A.1 to A.79 of table A.

Table 80: Compounds of the formula (Id) wherein $R_1$ is sec-butyl or isopropyl, A-B is —$CH_2$—$CH_2$—, Q is H and the combination of the substituents $R_2$ and $R_3$ for each compound corresponds to a line A.1 to A.79 of table A.

Table 81: Compounds of the formula (Id) wherein $R_1$ is cyclohexyl, A-B is —CH=CH—, Q is TBDMS and the combination of the substituents $R_2$ and $R_3$ for each compound corresponds to a line A.1 to A.79 of table A.

Table 82: Compounds of the formula (Id) wherein $R_1$ is cyclohexyl, A-B is —$CH_2$—$CH_2$—, Q is TBDMS and the combination of the substituents $R_2$ and $R_3$ for each compound corresponds to a line A.1 to A.79 of table A.

Table 83: Compounds of the formula (Id) wherein $R_1$ is cyclohexyl, A-B is —CH=CH—, Q is H and the combination of the substituents $R_2$ and $R_3$ for each compound corresponds to a line A.1 to A.79 of table A.

Table 84: Compounds of the formula (Id) wherein $R_1$ is cyclohexyl, A-B is —$CH_2$—$CH_2$—, Q is H and the combination of the substituents $R_2$ and $R_3$ for each compound corresponds to a line A.1 to A.79 of table A.

Table 85: Compounds of the formula (Id) wherein $R_1$ is 1-methyl-butyl, A-B is —CH=CH—, Q is TBDMS and the combination of the substituents $R_2$ and $R_3$ for each compound corresponds to a line A.1 to A.79 of table A.

Table 86: Compounds of the formula (Id) wherein $R_1$ is 1-methyl-butyl, A-B is —$CH_2$—$CH_2$—, Q is TBDMS and the combination of the substituents $R_2$ and $R_3$ for each compound corresponds to a line A.1 to A.79 of table A.

Table 87: Compounds of the formula (Id) wherein $R_1$ is 1-methyl-butyl, A-B is —CH=CH—, Q is H and the combination of the substituents $R_2$ and $R_3$ for each compound corresponds to a line A.1 to A.79 of table A.

Table 88: Compounds of the formula (Id) wherein $R_1$ is 1-methyl-butyl, A-B is —$CH_2$—$CH_2$—, Q is H and the combination of the substituents $R_2$ and $R_3$ for each compound corresponds to a line A.1 to A.79 of table A.

Table 89: Compounds of the formula (Id) wherein $R_1$ is ethyl, A-B is —CH=CH—, Q is TBDMS and the combination of the substituents $R_2$ and $R_3$ for each compound corresponds to a line A.1 to A.79 of table A.

Table 90: Compounds of the formula (Id) wherein $R_1$ is ethyl, A-B is —$CH_2$—$CH_2$—, Q is TBDMS and the combination of the substituents $R_2$ and $R_3$ for each compound corresponds to a line A.1 to A.79 of table A.

Table 91: Compounds of the formula (Id) wherein $R_1$ is ethyl, A-B is —CH=CH—, a is H and the combination of the substituents $R_2$ and $R_3$ for each compound corresponds to a line A.1 to A.79 of table A.

Table 92: Compounds of the formula (Id) wherein $R_1$ is ethyl, A-B is —$CH_2$—$CH_2$—, Q is H and the combination of the substituents $R_2$ and $R_3$ for each compound corresponds to a line A.1 to A.79 of table A.

Table 93: Compounds of the formula (Id) wherein $R_1$ is methyl, A-B is —CH=CH—, Q is TBDMS and the combination of the substituents $R_2$ and $R_3$ for each compound corresponds to a line A.1 to A.79 of table A.

Table 94: Compounds of the formula (Id) wherein $R_1$ is methyl, A-B is —$CH_2$—$CH_2$—, Q is TBDMS and the combination of the substituents $R_2$ and $R_3$ for each compound corresponds to a line A.1 to A.79 of table A.

Table 95: Compounds of the formula (Id) wherein $R_1$ is methyl, A-B is —CH=CH—, Q is H and the combination of the substituents $R_2$ and $R_3$ for each compound corresponds to a line A.1 to A.79 of table A.

Table 96: Compounds of the formula (Id) wherein $R_1$ is methyl, A-B is —$CH_2$—$CH_2$—, Q is H and the combination of the substituents $R_2$ and $R_3$ for each compound corresponds to a line A.1 to A.79 of table A.

Table 97: Compounds of the formula (Id) wherein $R_1$ is i-propyl, A-B is —CH=CH—, Q is TBDMS and the combination of the substituents $R_2$ and $R_3$ for each compound corresponds to a line A.1 to A.79 of table A.

Table 98: Compounds of the formula (Id) wherein $R_1$ is i-propyl, A-B is —$CH_2$—$CH_2$—, Q is TBDMS and the combination of the substituents $R_2$ and $R_3$ for each compound corresponds to a line A.1 to A.79 of table A.

Table 99: Compounds of the formula (Id) wherein $R_1$ is i-propyl, A-B is —CH=CH—, Q is H and the combination of the substituents $R_2$ and $R_3$ for each compound corresponds to a line A.1 to A.79 of table A.

Table 100: Compounds of the formula (Id) wherein $R_1$ is i-propyl, A-B is —$CH_2$—$CH_2$—, Q is H and the combination of the substituents $R_2$ and $R_3$ for each compound corresponds to a line A.1 to A.79 of table A.

Formulation Examples for Use in Crop Protection
(%=Percent by Weight)

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Mixing finely ground active ingredient and additives gives an emulsifiable concentrate which yields emulsions of the desired concentration on dilution with water.

| Example F2: Solutions | a) | b) | c) | d) |
|---|---|---|---|---|
| active ingredient | 80% | 10% | 5% | 95% |
| ethylene glycol monomethyl ether | — | 20% | — | — |
| polyethylene glycol (MW 400) | — | 70% | — | — |
| N-methylpyrrolid-2-one | 20% | — | — | — |
| epoxidised coconut oil | — | — | 1% | 5% |
| petroleum ether (boiling range: 160-190°) | — | — | 94% | — |

Mixing finely ground active ingredient and additives gives a solution suitable for use in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier mixture and the solvent is evaporated off in vacuo.

| Example F4: Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnapthalesesulfonate | — | 6% | 10% |
| octylphenol polyethylene glycol ether (7-8 mol EO) | — | 2% | — |
| highly dispersed silicic acid | 5% | 10% | 10% |
| kaolin | 62% | 27% | — |

Active ingredient and additives are mixed together and the mixture is ground in a suitable mill, yielding wettable powders that can be diluted with water to form suspensions of the desired concentration.

| Example F5: Emulsifiable concentrate | |
|---|---|
| active ingredient | 10% |
| octylphenol polyethylene glycol ether (4-5 mol EO) | 3% |
| calcium dodecylbenzenesulfonate | 3% |
| castor oil polyethylene glycol ether (36 mol EO) | 4% |
| cyclohexanone | 30% |
| xylene mixture | 50% |

Mixing finely ground active ingredient and additives gives an emulsifiable concentrate which yields emulsions of the desired concentration on dilution with water.

| Example F6: Extruder granules | |
|---|---|
| active ingredient | 10% |
| sodium lignosulfonate | 2% |
| carboxymethylcellulose | 1% |
| kaolin | 87% |

Active ingredient and additives are mixed together, the mixture is ground, moistened with water, extruded and granulated and the granules are dried in a stream of air.

| Example F7: Coated granules | |
|---|---|
| active ingredient | 3% |
| polyethylene glycol (MW 200) | 3% |
| kaolin | 94% |

Uniform application of the finely ground active ingredient to the kaolin moistened with polyethylene glycol in a mixer yields non-dusty coated granules.

| Example F8: Suspension concetrate | |
|---|---|
| active ingredient | 40% |
| ethylene glycol | 10% |
| nonylphenol polyethylene glycol ether (15 mol EO) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

Mixing finely ground active ingredient and additives gives a suspension concentrate which yields suspensions of the desired concentration on dilution with water.

BIOLOGICAL EXAMPLES

Example B1

Action Against *Spodoptera littoralis*

Young soybean plants are sprayed with an aqueous emulsion spray mixture comprising 12.5 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

The compounds of tables exhibit good activity in this test. Especially the compounds 1.5, 1.6, 2.6, 3.2, 3.5, 3.6, 3.8, 3.19, 4.8 and 4.18 exhibit an activity of over 80% in this test.

Example B2

Action Against *Spodoptera littoralis*, Systemic

Maize seedlings are placed in the test solution. 6 days later, the leaves are cut off, placed on moist filter paper in a petri dish and infested with 12 to 15 *Spodoptera littoralis* larvae in the $L_1$ stage. 4 days later, the percentage reduction in population (% activity) is determined by comparing the number of dead caterpillars on treated plants with that on untreated plants.

The compounds of tables exhibit good activity in this test. Especially the compounds 2.6, 3.6, 3.19, 4.8 and 4.18 exhibit an activity of over 80% in this test.

Example B3

Action against *Heliothis virescens*

30-35 eggs of *Heliothis virescens*, from 0 to 24 hours old, are placed on filter paper in a petri dish on a layer of artificial nutrient. 0.8 ml of the test solution is then pipetted onto the filter paper. Evaluation is made 6 days later. The percentage reduction in population (% activity) is determined by comparing the number of dead eggs and larvae on treated plants with that on untreated plants. Especially the compounds 1.5, 1.6 and 4.8 exhibit an activity of over 80% in this test.

The compounds of tables exhibit good activity in this test.

Example B4

Action Against *Plutella xylostella* Caterpillars

Young cabbage plants are sprayed with an aqueous emulsion spray mixture comprising 12.5 ppm of test compound. After the spray-coating has dried, the cabbage plants are populated with 10 caterpillars of *Plutella xylostella* in the first stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

The compounds of tables exhibit good activity in this test. Especially the compounds 2.5, 2.8, 4.5, 4.6 and 4.8 exhibit an activity of over 80% in this test.

Example B5

Action Against *Diabrotica balteata*

Maize seedlings are sprayed with an aqueous emulsion spray mixture comprising 12.5 ppm of the test compound and, after the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants.

The compounds of tables exhibit good activity in this test. In particular, compounds 1.5, 1.6, 2.6 and 4.8 are more than 80% effective.

Example B6

Action Against *Tetranychus urticae*

Young bean plants are populated with a mixed population of *Tetranychus urticae* and sprayed one day later with an aqueous emulsion spray mixture comprising 12.5 ppm of test compound. The plants are incubated for 6 days at 25° C. and subsequently evaluated. The percentage reduction in population (% activity) is determined by comparing the number of dead eggs, larvae and adults on the treated plants with that on untreated plants.

The compounds of tables exhibit good activity in this test. In particular, compounds 1.5, 1.6, 2.6, 3.2, 3.5, 3.6, 3.8, 3.19, 4.8 and 4.18 are more than 80% effective.

What is claimed is:
1. A compound of formula (I), wherein
is 0 or 1;
A-B is —CH═CH— or —CH$_2$—CH$_2$—;
R$_1$ is C$_1$-C$_{12}$-alkyl, C$_3$-C$_8$-cycloalkyl or C$_2$-C$_{12}$-alkenyl;
R$_2$ is C$_1$-C$_{12}$-alkyl, C$_2$-C$_{12}$-alkenyl; or C$_2$-C$_{12}$-alkinyl; or C$_1$-C$_{12}$-alkyl, C$_2$-C$_{12}$-alkenyl or C$_2$-C$_{12}$-alkinyl, which are substituted with one to five substituents selected from the group consisting of OH, halogen, CN, —N$_3$, —NO$_2$, C$_3$-C$_8$-cycloalkyl which is optionally substituted with one to three C$_1$-C$_6$-alkyl-groups, C$_3$-C$_8$-cycloalkenyl which is optionally substituted with one to three C$_1$-C$_6$-alkyl-groups, norbornylenyl-, C$_3$-C$_8$-halocycloalkyl, C$_1$-C$_{12}$-alkoxy, C$_1$-C$_6$-alkoxy-C$_1$-C$_6$-alkoxy, C$_3$-C$_8$-cycloalkoxy, C$_1$-C$_{12}$-haloalkoxy, C$_1$-C$_{12}$-alkylthio, C$_3$-C$_8$-cycloalkylthio, C$_1$-C$_{12}$-haloalkylthio, C$_1$-C$_{12}$-alkylsulfinyl, C$_3$-C$_8$-cycloalkylsulfinyl, C$_1$-C$_{12}$-haloalkylsulfinyl, C$_3$-C$_8$-halocycloalkylsulfinyl, C$_1$-C$_{12}$-alkylsulfonyl, C$_3$-C$_8$-cycloalkylsulfonyl, C$_1$-C$_{12}$-haloalkylsulfonyl, C$_3$-C$_8$-halocycloalkylsulfonyl, —NR$_4$R$_6$, —X—C(═Y)—R$_4$, —X—C(═Y)—Z—R$_4$, —P(═O)(OC$_1$-C$_6$-alkyl)$_2$, aryl, heterocyclyl, aryloxy, arylthio and heterocyclyloxy; wherein the aryl, heterocyclyl, aryloxy, arylthio and heterocyclyloxy groups are optionally depending on the substitution possibilities on the ring-substituted with one to five substituents selected form the group consisting of OH, Halogen, CN, $NO_2$, $C_1$-$C_{12}$-alkyl, $C_3$-$C_8$-Cycloalkyl, $C_1$-$C_{12}$-Haloalkyl, $C_1$-$C_{12}$-alkoxy, $C_1$-$C_{12}$-Haloalkoxy, $C_1$-$C_{12}$alkylthio, $C_1$-$C_{12}$-haloalkylthio, $C_1$-$C_6$-alkoxy-$C_1$-$C_6$alkyl, $C_2$-$C_8$-alkenyl, $C_2$-$C_8$-alkinyl, Si($C_1$-$C_{12}$-alkyl)$_3$, —X—C(=Y)—$R_4$, —X—C(=Y)—Z—$R_4$, aryl, aryloxy, heterocyclyl and heterocyclyloxy; or $R_2$ is aryl, heterocyclyl $C_3$-$C_8$-Cycloalkyl, $C_3$-$C_8$-Cycloalkenyl; or aryl, heterocyclyl $C_3$-$C_8$-Cyclo-alkyl or $C_3$-$C_8$-Cycloalkenyl, which are optionally depending on the substitution possibilities on the ring-substituted with one to five substituents selected from the group consisting of OH, halogen, CN, $NO_2$, $C_1$-$C_{12}$-alkyl, $C_3$-$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, dimethylamino-$C_1$-$C_6$-alkoxy, $C_2$-$C_8$-alkenyl, $C_2$-$C_8$-alkinyl, methylendioxy, aryl, aryloxy, heterocyclyl and heterocyclyloxy; $R_3$ is $C_3$-$C_8$-alkyl;

X is O, $NR_5$ or a bond;

Y is O or S;

Z is O, S or $NR_5$ $R_4$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution—possibilities—optionally substituted in the ring with one to five substituents selected from the group consisting of halogen, $C_1$-$C_6$-alkoxy, $C_1$-$C_6$-haloalkyl and $C_1$-$C_6$-haloalkoxy;

$R_5$ is H, $C_1$-$C_8$-alkyl, $C_3$-$C_8$-cycloalkyl, $C_2$-$C_8$-alkenyl, $C_2$-$C_8$-alkinyl, benzyl or —C(=O)—$C_1$-$C_{12}$-alkyl;

$R_6$ is H, $C_1$-$C_{12}$-alkyl which is optionally substituted with halogen, $C_1$-$C_6$-alkoxy, CN, $C_2$-$C_8$-alkenyl, $C_2$-$C_8$-haloalkenyl, $C_2$-$C_8$-alkinyl, $C_1$-$C_{12}$-Haloalkenyl, —X—C(=Y)—$R_9$, —X—C(=Y)—Z—$R_9$, —$SO_2$—$R_9$, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution—possibilities optionally substituted in the ring with one to five substituents selected from the group consisting of halogen, $C_1$-$C_6$-alkoxy, $C_1$-$C_6$-haloalkyl or $C_1$-$C_6$-haloalkoxy; or $R_4$ and $R_6$ together are a three- to five membered alkylene bridge, wherein one of the methylene groups may be replaced by O, S or $SO_2$; and $R_9$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are depending on the substitution possibilities optionally substituted in the ring with one to five substituents selected from the group consisting of halogen, $C_1$-$C_6$-alkoxy, $C_1$-$C_6$-haloalkyl and $C_1$-$C_6$-haloalkoxy;

and, where applicable, to E/Z isomers, mixtures of E/Z isomers and/or tautomers, in each case in free form or in salt form.

2. A compound of formula (I),

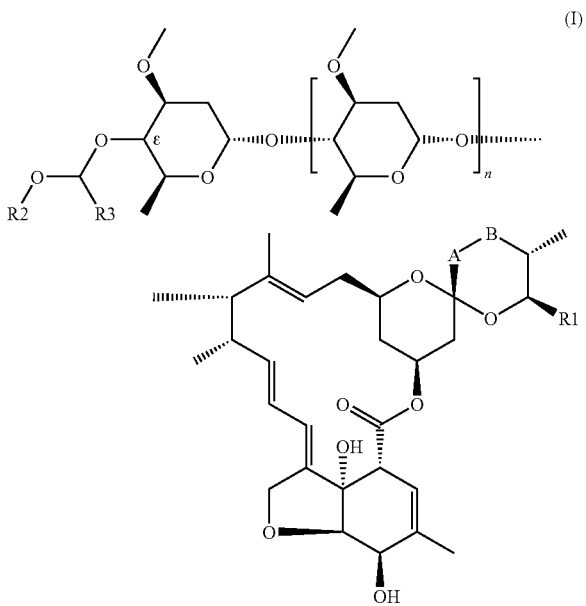

(I)

wherein n is 0 or 1;

A-B is —CH=CH— or —$CH_2$—$CH_2$—;

$R_1$ is $C_1$-$C_{12}$-alkyl, $C_3$-$C_8$-cycloalkyl or $C_2$-$C_{12}$-alkenyl;

$R_2$ is $C_1$-$C_{12}$-alkyl, $C_2$-$C_{12}$-alkenyl, $C_2$-$C_{12}$-alkinyl; or $C_1$-$C_{12}$-alkyl, $C_2$-$C_{12}$-alkenyl or $C_2$-$C_{12}$-alkinyl, which are substituted with one to five substituents selected from the group consisting of OH, halogen, ON, —$N_3$, —$NO_2$, $C_3$-$C_8$-cycloalkyl which is optionally substituted with one to three $C_1$-$C_6$-alkyl-groups, $C_3$-$C_8$-cycloalkenyl which is optionally substituted with one to three $C_1$-$C_6$-alkyl-groups, norbornylenyl-, $C_3$-$C_8$-halocycloalkyl, $C_1$-$C_{12}$-alkoxy, $C_1$-$C_6$-alkoxy-$C_1$-$C_6$-alkoxy, $C_3$-$C_8$-cycloalkoxy, $C_1$-$C_{12}$-haloalkoxy, $C_1$-$C_{12}$-alkylthio, $C_3$-$C_8$-cycloalkylthio, $C_1$-$C_{12}$-haloalkylthio, $C_1$-$C_{12}$-alkylsulfinyl, $C_3$-$C_8$-cycloalkylsulfinyl, $C_1$-$C_{12}$-haloalkylsulfinyl, $C_3$-$C_8$-halocycloalkylsulfinyl, $C_1$-$C_{12}$-alkylsulfonyl, $C_3$-$C_8$-cycloalkylsulfonyl, $C_1$-$C_{12}$-haloalkylsulfonyl, $C_3$-$C_8$-halocycloalkylsulfonyl, —$NR_4R_6$, —X—C(=Y)—$R_4$, —X—C(=Y)—Z—$R_4$, —P(=O)(O$C_1$-$C_6$-alkyl)$_2$, aryl, heterocyclyl, aryloxy, arylthio and heterocyclyloxy: wherein the aryl, heterocyclyl, aryloxy, arylthio and heterocyclyloxy groups are optionally depending on the substitution possibilities on the ring substituted with one to five substituents selected form the group consisting of OH, Halogen, CN, $NO_2$, $C_1$-$C_{12}$-alkyl, $C_3$-$C_8$-Cycloalkyl, $C_1$-$C_{12}$-Haloalkyl, $C_1$-$C_{12}$-alkoxy, $C_1$-$C_{12}$-Haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, Si($C_1$-$C_{12}$-alkyl)$_3$, —X—C(=Y)—$R_4$, —X—C(=Y)—Z—$R_4$, aryl, aryloxy, heterocyclyl and heterocyclyloxy; or $R_2$ is aryl, heterocyclyl $C_3$-$C_8$-Cycloalkyl, $C_3$-$C_8$-Cycloalkenyl; or aryl, heterocyclyl $C_3$-$C_8$-Cyclo-alkyl or $C_3$-$C_8$-Cycloalkenyl, which are optionally depending on the substitution possibilities on the ring—substituted with one to five substituents selected from the group consisting of OH, halogen, CN, $NO_2$, $C_1$-$C_{12}$-alkyl, $C_3$-$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, dimethylamino-$C_1$-

$C_6$-alkoxy, $C_2$-$C_8$-alkenyl, $C_2$-$C_8$-alkinyl, methylendioxy, aryl, aryloxy, heterocyclyl and heterocyclyloxy;

$R_3$ is $C_1$-$C_8$-alkyl which is substituted with one to five substituents selected from the group consisting of OH, halogen, ON, —$N_3$, —$NO_2$, $C_3$-$C_8$-cycloalkyl which is optionally substituted with one to three $C_1$-$C_6$-alkyl groups, norbornylenyl-, $C_3$-$C_8$-cycloalkenyl which is optionally substituted with one to three methyl groups; $C_3$-$C_8$-halocycloalkyl, $C_3$-$C_8$-cycloalkoxy, $C_1$-$C_{12}$-haloalkoxy, $C_1$-$C_{12}$-alkylthio, aryl, heterocyclyl, arylthio or heterocyclyloxy; wherein the aryl, heterocyclyl, arylthio and heterocyclyloxy groups are optionally—depending on the substitution possibilities on the ring—substituted with one to five substituents selected form the group consisting of OH, Halogen, CN, $NO_2$, $C_1$-$C_{12}$-alkyl, $C_3$-$C_8$-cycloalkyl, $C_1$-$C_{12}$-haloalkyl, $C_1$-$C_{12}$-alkoxy, $C_1$-$C_{12}$-haloalkoxy, $C_1$-$C_{12}$-alkylthio, $C_1$-$C_{12}$-haloalkylthio, $C_1$-$C_6$-alkoxy-$C_1$-$C_6$-alkyl, $C_2$-$C_8$-alkenyl, $C_2$-$C_8$-alkinyl, $Si(C_1$-$C_{12}$-alkyl$)_3$, —X—C(=Y)—$R_4$, —X—O(=Y)—Z—$R_4$, aryl, aryloxy, heterocyclyl and heterocyclyloxy;

X is O, $NR_5$ or a bond;

Y is O or S;

Z is O, S or $NR_5$ $R_4$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are—depending on the substitution possibilities—optionally substituted in the ring with one to five substituents selected from the group consisting of halogen, $C_1$-$C_6$-alkoxy, $C_1$-$C_6$-haloalkyl and $C_1$-$C_6$-haloalkoxy;

$R_5$ is H, $C_1$-$C_8$-alkyl, $C_3$-$C_8$-cycloalkyl, $C_2$-$C_8$-alkenyl, $C_2$-$C_8$-alkinyl, benzyl or —C(=O)—$C_1$-$C_{12}$-alkyl;

$R_6$ is H, $C_1$-$C_{12}$-alkyl which is optionally substituted with halogen, $C_1$-$C_6$-alkoxy, ON, $C_2$-$C_8$-alkenyl, $C_2$-$C_8$-haloalkenyl, $C_2$-$C_8$-alkinyl, $C_1$-$C_{12}$-Haloalkenyl, —X—C(=Y)—$R_9$, —X—C(=Y)—Z—$R_9$, —$SO_2$—$R_9$, aryl, heterocyclyl, aryl-$C_1$-$C_{12}$-alkyl, heterocyclyl-$C_1$-$C_{12}$-alkyl; or aryl, heterocyclyl, aryl-$C_1$-$C_{12}$-alkyl or heterocyclyl-$C_1$-$C_{12}$-alkyl, which are depending on the substitution possibilities optionally substituted in the ring with one to five substituents selected from the group consisting of halogen, $C_1$-$C_6$-alkoxy, $C_1$-$C_6$-haloalkyl or $C_1$-$C_6$-haloalkoxy; or $R_4$ and $R_6$ to ether are a three- to five membered alkylene bridge, wherein one of the methylene groups may be replaced by O, S or $SO_2$; and $R_9$ is H, $C_1$-$C_{12}$-alkyl which is optionally substituted with one to five substituents selected from the group consisting of halogen, hydroxy, $C_1$-$C_6$-alkoxy and CN; $C_2$-$C_8$-alkenyl, $C_2$-$C_8$-alkinyl, aryl, heterocyclyl-$C_1$-$C_{12}$-alkyl, heterocyclyl-$C_1$-$C_{19}$-alkyl; or a aryl, heterocyclyl, aryl-$C_1$-$C_{12}$-alkyl or heterocyclyl-$C_1$-$C_{12}$-alkyl, which are depending on the substitution possibilities optionally substituted in the ring with one to five substituents selected from the group consisting of halogen, $C_1$-$C_6$-alkoxy, $C_1$-$C_6$-haloalkyl and $C_1$-$C_6$-haloalkoxy;

and, where applicable, to E/Z isomers, mixtures of E/Z isomers and/or tautomers, in each case in free form or in salt form.

3. A compound according to claim 1 of the formula (I), wherein $R_3$ is $C_7$-$C_8$ alkyl.

* * * * *